US010300036B2

(12) United States Patent
Zhang et al.

(10) Patent No.: US 10,300,036 B2
(45) Date of Patent: May 28, 2019

(54) COMPOSITIONS AND METHODS FOR TREATING AND PREVENTING LUNG INJURY

(71) Applicant: ARIZONA BOARD OF REGENTS on behalf of THE UNIVERSITY OF ARIZONA, Tucson, AZ (US)

(72) Inventors: Donna D. Zhang, Tucson, AZ (US); Georg T. Wondrak, Tucson, AZ (US); Joe G. N. Garcia, Tucson, AZ (US); Ting Wang, Tucson, AZ (US)

(73) Assignee: ARIZONA BOARD OF REGENTS on behalf of THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/765,777

(22) PCT Filed: Oct. 5, 2016

(86) PCT No.: PCT/US2016/055525
§ 371 (c)(1),
(2) Date: Apr. 4, 2018

(87) PCT Pub. No.: WO2017/062472
PCT Pub. Date: Apr. 13, 2017

(65) Prior Publication Data
US 2018/0280338 A1    Oct. 4, 2018

Related U.S. Application Data

(60) Provisional application No. 62/237,153, filed on Oct. 5, 2015.

(51) Int. Cl.
*A61K 31/232* (2006.01)
*A61K 36/185* (2006.01)
*A61K 9/00* (2006.01)

(52) U.S. Cl.
CPC ............ *A61K 31/232* (2013.01); *A61K 9/007* (2013.01); *A61K 36/185* (2013.01)

(58) Field of Classification Search
CPC ........ A61Q 19/00; A61K 31/232; A61P 11/00
See application file for complete search history.

(56) References Cited

U.S. PATENT DOCUMENTS

2009/0196921 A1    8/2009    Ebel et al.
2013/0005666 A1    1/2013    Ratan et al.

OTHER PUBLICATIONS

SAle product bixin from Alibaba.com, 2014.*
Sale product bixin from Sigma-Aldrich, 2014.*
Tao et al., Free Radical and Medicine, 89:690-700, 2015.*
Cho et al., Antioxidants & Pedox Signaling, 2012, 17(8): 1066-1082.*

Auttachoat, W., Germolec, D.R., Smith, M.J., White, K.L., Jr. & Guo, T.L. Contact sensitizing potential of annatto extract and its two primary color components, cis-bixin and norbixin, in female BALB/c mice. Food Chem Toxicol 49, 2638-44 (2011).
Bertram, J.S. et al. Diverse carotenoids protect against chemically induced neoplastic transformation. Carcinogenesis 12, 671-8 (1991).
Chapman, K.E. et al. Cyclic mechanical strain increases reactive oxygen species production in pulmonary epithelial cells. Am J Physiol Lung Cell Mol Physiol 289, L834-41 (2005).
Chen, H. et al. NFkB and Nrf2 in esophageal epithelial barrier function. Tissue Barriers 1, e27463 (2013).
Chiste, R.C. et al. In vitro scavenging capacity of annatto seed extracts against reactive oxygen and nitrogen species. Food Chem 127, 419-26 (2011).
Cho, H.Y. & Kleeberger, S.R. Nrf2 protects against airway disorders. Toxicol Appl Pharmacol 244, 43-56 (2010).
Cho, H.Y., Reddy, S.P., Yamamoto, M. & Kleeberger, S.R. The transcription factor NRF2 protects against pulmonary fibrosis. FASEB J 18, 1258-60 (2004).
Di Mascio, P., Devasagayam, T.P., Kaiser, S. & Sies, H. Carotenoids, tocopherols and thiols as biological singlet molecular oxygen quenchers. Biochem Soc Trans 18, 1054-6 (1990).
Dinkova-Kostova, A.T. et al. Direct evidence that sulfhydryl groups of Keap1 are the sensors regulating induction of phase 2 enzymes that protect against carcinogens and oxidants. Proc Natl Acad Sci U S A 99, 11908-13 (2002).
Dos Santos, C.C. & Slutsky, A.S. Invited review: mechanisms of ventilator-induced lung injury: a perspective. J Appl Physiol (1985) 89, 1645-55 (2000).
Dos Santos, G.C. et al. Protective effect of bixin on cisplatin-induced genotoxicity in PC12 cells. Food Chem Toxicol 50, 335-40 (2012).
Fan, E., Villar, J. & Slutsky, A.S. Novel approaches to minimize ventilator-induced lung injury. BMC Med 11, 85 (2013).
Giuliano, G., Rosati, C. & Bramley, P.M. To dye or not to dye: biochemistry of annatto unveiled. Trends Biotechnol 21, 513-6 (2003).
International Search Report and Written Opinion, International Patent Application No. PCT/US2016/055525, dated Dec. 8, 2016, 13 pages.
Jafari, B., Ouyang, B., Li, L.F., Hales, C.A. & Quinn, D.A. Intracellular glutathione in stretch-induced cytokine release from alveolar type-2 like cells. Respirology 9, 43-53 (2004).
Jaramillo, M.C. & Zhang, D.D. The emerging role of the Nrf2-Keap1 signaling pathway in cancer. Genes Dev 27, 2179-91 (2013).
Jiang, T. et al. Nrf2 suppresses lupus nephritis through inhibition of oxidative injury and the NF-kappaB-mediated inflammatory response. Kidney Int (2013).
Kaulmann, A. & Bohn, T. Carotenoids, inflammation, and oxidative stress—implications of cellular signaling pathways and relation to chronic disease prevention. Nutr Res 34, 907-29 (2014).

(Continued)

*Primary Examiner* — Rei Tsang Shiao
(74) *Attorney, Agent, or Firm* — Casimir Jones, S.C.; Tanya A. Arenson

(57) ABSTRACT

Provided herein are compositions and methods for treating and preventing lung injury (e.g. ventilation induced lung injury). In particular, the invention relates to compositions and methods for treating and preventing airway disease by activating the NRF2 pathway.

7 Claims, 21 Drawing Sheets
Specification includes a Sequence Listing.

(56) References Cited

OTHER PUBLICATIONS

Kensler, T.W., Wakabayashi, N. & Biswal, S. Cell survival responses to environmental stresses via the Keap1-Nrf2-ARE pathway. Annu Rev Pharmacol Toxicol 47, 89-116 (2007).
Kobayashi, A. et al. Oxidative stress sensor Keap1 functions as an adaptor for Cul3-based E3 ligase to regulate proteasomal degradation of Nrf2. Mol Cell Biol 24, 7130-9 (2004).
Kuchnicka, K. & Maciejewski, D. Ventilator-associated lung injury. Anaesthesiol Intensive Ther 45, 164-70 (2013).
Lau, A. et al. A noncanonical mechanism of Nrf2 activation by autophagy deficiency: direct interaction between Keap1 and p62. Mol Cell Biol 30, 3275-85 (2010).
Lau, A., Whitman, S.A., Jaramillo, M.C. & Zhang, D.D. Arsenic-mediated activation of the Nrf2-Keap1 antioxidant pathway. J Biochem Mol Toxicol 27, 99-105 (2013).
Letsiou, E. et al. Differential and opposing effects of imatinib on LPS- and ventilator-induced lung injury. Am J Physiol Lung Cell Mol Physiol 308, L259-69 (2015).
Levy, L.W., Regalado, E., Navarrete, S. & Watkins, R.H. Bixin and norbixin in human plasma: determination and study of the absorption of a single dose of Annatto food color. Analyst 122, 977-80 (1997).
Liu, Y.Y. et al. Role for nuclear factor-kappaB in augmented lung injury because of interaction between hyperoxia and high stretch ventilation. Transl Res 154, 228-40 (2009).
Meakin, P.J. et al. Susceptibility of Nrf2-null mice to steatohepatitis and cirrhosis upon consumption of a high-fat diet is associated with oxidative stress, perturbation of the unfolded protein response, and disturbance in the expression of metabolic enzymes but not with insulin resistance. Mol Cell Biol 34, 3305-20 (2014).
Mirzapoiazova, T. et al. Non-muscle myosin light chain kinase isoform is a viable molecular target in acute inflammatory lung injury. Am J Respir Cell Mol Biol 44, 40-52 (2011).
Moreira, P.R. et al. Protective effect of bixin on carbon tetrachloride-induced hepatotoxicity in rats. Biol Res 47, 49 (2014).
Moreno-Vinasco, L. et al. Nicotinamide phosphoribosyltransferase inhibitor is a novel therapeutic candidate in murine models of inflammatory lung injury. Am J Respir Cell Mol Biol 51, 223-8 (2014).
Nickles, H.T. et al. Mechanical ventilation causes airway distension with proinflammatory sequelae in mice. Am J Physiol Lung Cell Mol Physiol 307, L27-37 (2014).
Oudin, S. & Pugin, J. Role of MAP kinase activation in interleukin-8 production by human BEAS-2B bronchial epithelial cells submitted to cyclic stretch. Am J Respir Cell Mol Biol 27, 107-14 (2002).
Papaihgari, S. et al. Genetic and pharmacologic evidence links oxidative stress to ventilator-induced lung injury in mice. Am J Respir Crit Care Med 176, 1222-35 (2007).
Reddy, N.M., Potteti, H.R., Mariani, T.J., Biswal, S. & Reddy, S.P. Conditional deletion of Nrf2 in airway epithelium exacerbates acute lung injury and impairs the resolution of inflammation. Am J Respir Cell Mol Biol 45, 1161-8 (2011).
Reddy, NM et al. The Triterpenoid CDDO-Imidazolide Confers Potent Protection against Hyperoxic Acute Lung Injury in Mice. American Journal of Respiratory and Critical Care Medicine, vol. 180, No. 9, 2009, pp. 867-874.
Reiss, L.K. et al. Interplay between nuclear factor erythroid 2-related factor 2 and amphiregulin during mechanical ventilation. Am J Respir Cell Mol Biol 51, 668-77 (2014).
Roehrs, M. et al. Bixin and norbixin have opposite effects on glycemia, lipidemia, and oxidative stress in streptozotocin-induced diabetic rats. Int J Endocrinol 2014, 839095 (2014).
Serpa Neto, A., Simonis, F.D. & Schultz, M.J. How to ventilate patients without acute respiratory distress syndrome? Curr Opin Crit Care 21, 65-73 (2015).
Serwer, L. et al. Systemic and Local Drug Delivery for Treating Diseases of the Central Nervous System in Rodent Models. Journal of Visualized Experiments, vol. 42, published Aug. 16, 2010, pp. 1-6.
Shen, T. et al. Plant extracts of the family Lauraceae: a potential resource for chemopreventive agents that activate the nuclear factor-erythroid 2-related factor 2/antioxidant response element pathway. Planta Med 80, 426-34 (2014).
Silva, C.R., Antunes, L.M. & Bianchi, M.L. Antioxidant action of bixin against cisplatin-induced chromosome aberrations and lipid peroxidation in rats. Pharmacol Res 43, 561-6 (2001).
Slutsky, A.S. & Ranieri, V.M. Ventilator-induced lung injury. N Engl J Med 369, 2126-36 (2013).
Stohs, S.J. Safety and efficacy of *Bixa orellana* (achiote, annatto) leaf extracts. Phytother Res 28, 956-60 (2014).
Surh, Y.J. Cancer chemoprevention with dietary phytochemicals. Nat Rev Cancer 3, 768-80 (2003).
Tanaka, T., Shnimizu, M. & Moriwaki, H. Cancer Chemoprevention by Carotenoids. Molecules 17, 3202-3242 (2012).
Tao, S. et al. Tanshinone I activates the Nrf2-dependent antioxidant response and protects against As(III)-induced lung inflammation in vitro and in vivo. Antioxid Redox Signal 19, 1647-61 (2013).
Tao, S., Justiniano, R., Zhang, D.D. & Wondrak, G.T. The Nrf2-inducers tanshinone I and dihydrotanshinone protect human skin cells and reconstructed human skin against solar simulated UV. Redox Biol 1, 532-41 (2013).
Tibodeau, J.D., Isham, C.R. & Bible, K.C. Annatto constituent cis-bixin has selective antimyeloma effects mediated by oxidative stress and associated with inhibition of thioredoxin and thioredoxin reductase. Antioxid Redox Signal 13, 987-97 (2010).
Vilar DDE, A. et al. Traditional uses, chemical constituents, and biological activities of *Bixa orellana* L.: a review. ScientificWorldJournal 2014, 857292 (2014).
Wang, X.J. et al. Activation of Nrf2 by arsenite and monomethylarsonous acid is independent of Keap1-C151: enhanced Keap1-Cul3 interaction. Toxicol Appl Pharmacol 230, 383-9 (2008).
Wondrak, G.T. et al. The cinnamon-derived dietary factor cinnamic aldehyde activates the Nrf2-dependent antioxidant response in human epithelial colon cells. Molecules 15, 3338-55 (2010).
Wright, B.J. Lung-protective ventilation strategies and adjunctive treatments for the emergency medicine patient with acute respiratory failure. Emerg Med Clin North Am 32, 871-87 (2014).
Wunsch, H. et al. The epidemiology of mechanical ventilation use in the United States. Crit Care Med 38, 1947-53 (2010).
Zhang, D.D. & Hannink, M. Distinct cysteine residues in Keap1 are required for Keap1-dependent ubiquitination of Nrf2 and for stabilization of Nrf2 by chemopreventive agents and oxidative stress. Mol Cell Biol 23, 8137-51 (2003).
Zhang, D.D., Lo, S.C., Cross, J.V., Templeton, D.J. & Hannink, M. Keap1 is a redox-regulated substrate adaptor protein for a Cul3-dependent ubiquitin ligase complex. Mol Cell Biol 24, 10941-53 (2004).
Zhang, L.X., Cooney, R.V. & Bertram, J.S. Carotenoids enhance gap junctional communication and inhibit lipid peroxidation in C3H/10T1/2 cells: relationship to their cancer chemopreventive action. Carcinogenesis 12, 2109-14 (1991).
Zhang, X. et al. Carotenoid inhibit proliferation and regulate expression of peroxisome proliferators-activated receptor gamma (PPARc) in K562 cancer cells. Archives of Biochemistry and Biophysics, vol. 512, 2011, pp. 96-106.
Zheng, Y. et al. Sulforaphane prevents pulmonary damage in response to inhaled arsenic by activating the Nrf2-defense response. Toxicol Appl Pharmacol 265, 292-9 (2012).

\* cited by examiner a Chemical structure b

C d a b

SEQUENCE LISTING

<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: synthetic

<400> SEQUENCE: 1
ctcagcatga tggacttgga        20

<210> SEQ ID NO 2
<211> LENGTH: 20
<212> TYPE: DNA
<213> ORGANISM: Artificial sequence
<220> FEATURE:
<223> OTHER INFORMATION: synthetic

<400> SEQUENCE: 2
tcttgcctcc aaaggatgtc        20

```
<210> SEQ ID NO 3
<211> LENGTH: 19
<212> TYPE: DNA
<213> ORGANISM: Artificial sequence
<220> FEATURE:
<223> OTHER INFORMATION: synthetic

<400> SEQUENCE: 3
gatcggctgc actgaactg                                                  19

<210> SEQ ID NO 4
<211> LENGTH: 20
<212> TYPE: DNA
<213> ORGANISM: Artificial sequence
<220> FEATURE:
<223> OTHER INFORMATION: synthetic

<400> SEQUENCE: 4
ggcagtgtga caggttgaag                                                 20

<210> SEQ ID NO 5
<211> LENGTH: 20
<212> TYPE: DNA
<213> ORGANISM: Artificial sequence
<220> FEATURE:
<223> OTHER INFORMATION: synthetic

<400> SEQUENCE: 5
gagcctgaat cgagcagaac                                                 20

<210> SEQ ID NO 6
<211> LENGTH: 20
<212> TYPE: DNA
<213> ORGANISM: Artificial sequence
<220> FEATURE:
<223> OTHER INFORMATION: synthetic

<400> SEQUENCE: 6
ctcggcttgg atgtgtacct                                                 20

<210> SEQ ID NO 7
<211> LENGTH: 20
<212> TYPE: DNA
<213> ORGANISM: Artificial sequence
<220> FEATURE:
<223> OTHER INFORMATION: synthetic

<400> SEQUENCE: 7
tcccatgcag tggagaagat                                                 20

<210> SEQ ID NO 8
<211> LENGTH: 20
<212> TYPE: DNA
<213> ORGANISM: Artificial sequence
<220> FEATURE:
<223> OTHER INFORMATION: synthetic

<400> SEQUENCE: 8
agctgtgcaa ctccaaggac                                                 20

<210> SEQ ID NO 9
<211> LENGTH: 20
<212> TYPE: DNA
<213> ORGANISM: Artificial sequence
<220> FEATURE:
<223> OTHER INFORMATION: synethtic
```

```
<400> SEQUENCE: 9
aaggccaacc gtgaaaagat                                               20

<210> SEQ ID NO 10
<211> LENGTH: 21
<212> TYPE: DNA
<213> ORGANISM: Artificial sequence
<220> FEATURE:
<223> OTHER INFORMATION: synthetic

<400> SEQUENCE: 10
gtggtacgac cagaggcata c                                             21
```

COMPOSITIONS AND METHODS FOR TREATING AND PREVENTING LUNG INJURY

CROSS-REFERENCE TO RELATED APPLICATIONS

This application is a Section 371 U.S. national stage entry of International Patent Application No. PCT/US2016/055525, International Filing Date Oct. 5, 2016 which claims priority to and the benefit of U.S. Provisional Application No. 62/237,153, filed Oct. 5, 2015, which are hereby incorporated by reference in their entireties.

FIELD OF THE INVENTION

Provided herein are compositions and methods for treating and preventing lung injury (e.g. ventilation induced lung injury). In particular, the invention relates to compositions and methods for treating and preventing airway disease by activating the NRF2 pathway.

INTRODUCTION

Mechanical ventilation (MV) is a life support therapy used to assist patients that have difficulty in breathing spontaneously, that present hypoxia or hypotension (Wright, B. J. Lung-protective ventilation strategies and adjunctive treatments for the emergency medicine patient with acute respiratory failure. Emerg Med Clin North Am 32, 871-87 (2014)). It is an intervention procedure for patients suffering from lung trauma, chronic obstructive pulmonary disease (COPD), acute respiratory distress syndrome (ARDS), apnea, severe asthma, or for patients under general anesthesia (Wunsch, H. et al. The epidemiology of mechanical ventilation use in the United States. Crit Care Med 38, 1947-53 (2010)).

Paradoxically, although MV is the only effective strategy to treat these conditions, it may also result in greater lung damage, referred to as ventilator-induced lung injury (VILI), and multi-organ failure that can compromise the patients' lives (Serpa Neto, A., Simonis, F. D. & Schultz, M. J. How to ventilate patients without acute respiratory distress syndrome? Curr Opin Crit Care 21, 65-73 (2015); Dos Santos, C. C. & Slutsky, A. S. Invited review: mechanisms of ventilator-induced lung injury: a perspective. J Appl Physiol (1985) 89, 1645-55 (2000)). VILI occurs as an effect of cyclic stretching and overdistension of the lung tissues, which cause severe inflammation and structural tissue damage ultimately leading to acute lung injury (ALI) (Letsiou, E. et al. Differential and opposing effects of imatinib on LPS- and ventilator-induced lung injury. Am J Physiol Lung Cell Mol Physiol 308, L259-69 (2015); Nickles, H. T. et al. Mechanical ventilation causes airway distension with proinflammatory sequelae in mice. Am J Physiol Lung Cell Mol Physiol 307, L27-37 (2014)). Additional factors that contribute to VILI are the disease or events that led to respiratory failure, and the parameters used in MV treatment (volume, pressure, and duration) (Fan, E., Villar, J. & Slutsky, A. S. Novel approaches to minimize ventilator-induced lung injury. BMC Med 11, 85 (2013)). Up to now there are no efficient pharmacological strategies to ameliorate the negative effects caused by MV, and only a conservative approach using a low tidal volume has been shown to cause less damage (Slutsky, A. S. & Ranieri, V. M. Ventilator-induced lung injury. N Engl J Med 369, 2126-36 (2013)).

VILI is characterized by a disruption of the alveolar-capillary barrier which increases permeability, thus causing edema, inflammatory leukocyte infiltration (mainly neutrophils), and hemorrhage (Moreno-Vinasco, L. et al. Nicotinamide phosphoribosyltransferase inhibitor is a novel therapeutic candidate in murine models of inflammatory lung injury. Am J Respir Cell Mol Biol 51, 223-8 (2014)). Stretch forces cause the release of inflammatory cytokines like IL6, IL8, IL1β, and TNFα by activation of the p38 MAPK pathway and of the transcription factor NF-κB (Oudin, S. & Pugin, J. Role of MAP kinase activation in interleukin-8 production by human BEAS-2B bronchial epithelial cells submitted to cyclic stretch. Am J Respir Cell Mol Biol 27, 107-14 (2002); Liu, Y. Y. et al. Role for nuclear factor-kappaB in augmented lung injury because of interaction between hyperoxia and high stretch ventilation. Transl Res 154, 228-40 (2009)). Cyclic stretch also generates reactive oxygen species (ROS) that further exacerbate VILI (Chapman, K. E. et al. Cyclic mechanical strain increases reactive oxygen species production in pulmonary epithelial cells. Am J Physiol Lung Cell Mol Physiol 289, L834-41 (2005)). These events are followed by the onset of an endogenous anti-inflammatory and anti-oxidative reaction to compensate for and attenuate VILI-derived inflammatory response and redox imbalance (Jafari, B., Ouyang, B., Li, L. F., Hales, C. A. & Quinn, D. A. Intracellular glutathione in stretch-induced cytokine release from alveolar type-2 like cells. Respirology 9, 43-53 (2004)).

Thus, agents to treat or prevent VILI are needed.

SUMMARY OF THE INVENTION

Mechanical ventilation (MV) is a therapeutic intervention widely used in the clinic to assist patients that have difficulty breathing due to lung edema, trauma, or general anesthesia. However, MV causes ventilator-induced lung injury (VILI), a condition characterized by increased permeability of the alveolar-capillary barrier that results in edema, hemorrhage, and neutrophil infiltration, leading to exacerbated lung inflammation and oxidative stress.

Experiments described herein demonstrated that bixin, a canonical NRF2 inducer, functions to ameliorate lung damage in a murine VILI model. In vitro, bixin was found to activate the NRF2 signaling pathway through blockage of ubiquitylation and degradation of NRF2 in a KEAP1-C151 dependent manner; intraperitoneal (IP) injection of bixin led to pulmonary upregulation of the NRF2 response in vivo. IP administration of bixin restored normal lung morphology and attenuated inflammatory response and oxidative DNA damage following MV. This observed beneficial effect of bixin derived from induction of the NRF2 cytoprotective response since it was only observed in Nrf2$^{+/+}$ but not in Nrf2$^{-/-}$ mice.

Accordingly, the present invention provides pharmacological agents for clinical use to prevent patients from lung injury during MV treatment, thus meeting a long unmet need in the art.

For example, in some embodiments, the present invention provides a method of treating or preventing ventilator-induced lung injury, comprising: administering at least one agent that activates an NRF2-mediated response to a subject prior to, during, or after mechanical ventilation. In some embodiments, the agent is bixin or a derivative, mimetic, pharmaceutically acceptable salts, solvates, and/or prodrugs thereof. In some embodiments, the agent activates said NRF2-mediated response by inhibiting KEAP1-mediated ubiquitination of NRF2. In some embodiments, the agent is administered directly to the lungs or systemically of the subject. In some embodiments, the administering prevents inflammation and oxidative DNA damage in the subject. In some embodiments, the administering treats or prevents acute lung injury in the subject. In some embodiments, the subject has lung trauma, chronic obstructive pulmonary disease (COPD), acute respiratory distress syndrome (ARDS), apnea, severe asthma, or is under general anesthesia.

Further embodiments provide the use of at least one agent that activates an NRF2-mediated response in the treatment or prevention of ventilator-induced lung injury in a subject prior to, during, or after mechanical ventilation.

Yet other embodiments, the present invention provides the use of at least one agent that activates an NRF2-mediated response in the preparation of a medicament for the treatment or prevention of ventilator-induced lung injury in a subject prior to, during, or after mechanical ventilation.

Still further embodiments provides a kit comprising a composition comprising an effective amount of an agent that activates an NRF2-mediated response (e.g., bixin or variant thereof), wherein the composition is capable of activating NRF2 pathway related activity, and instructions for administering the composition to a subject prior to, during, or after mechanical ventilation. In some embodiments, the bixin is formulated for pulmonary or systemic delivery.

Additional embodiments are described herein.

DEFINITIONS

Figure 1:
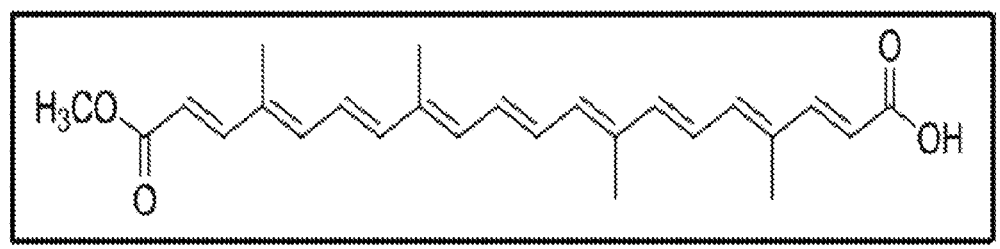
FIG. 1 shows that bixin upregulates the NRF2 signaling pathway. (a) Bixin chemical structure. (b) Cell viability was measured in H1299 cells treated with the indicated doses of bixin for 48 h. (c) H1299 cells were treated with the indicated doses of bixin for 4 h and 16 h, cell lysates were subjected to immunoblot analyses. (d) H1299 cells were treated with bixin (40 µM) for the indicated time, cell lysates were subjected to immunoblot analyses. * indicates the specific HO-1 band in H1299 cells. (e) H1299 cells were either left untreated (control, Ctrl) or treated with bixin (40 µM) for 4 h and 16 h, and mRNA was extracted.
Figure 1:
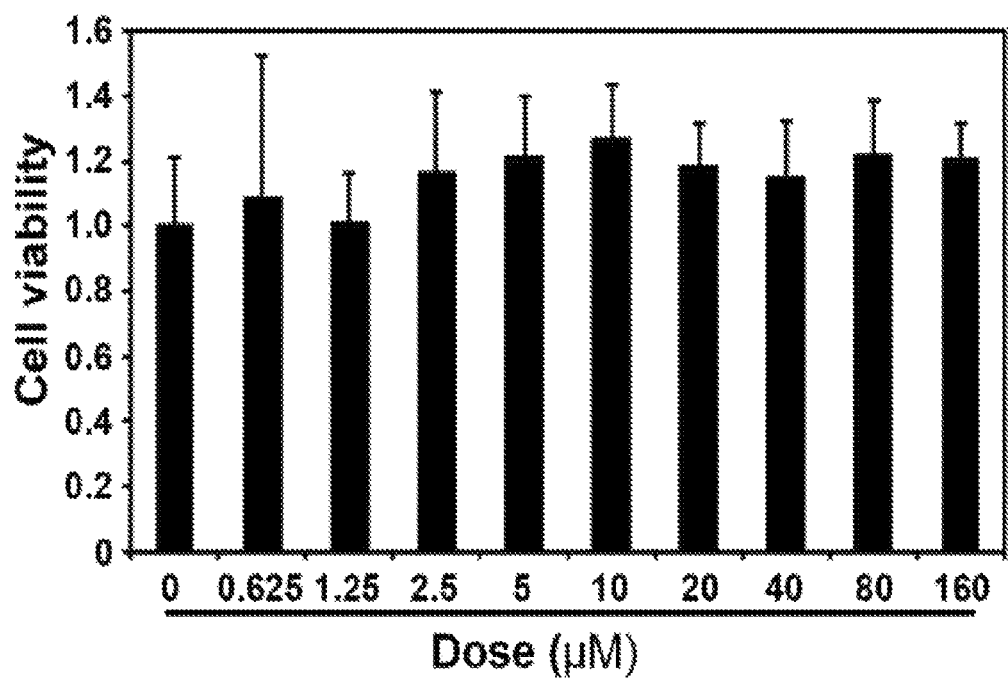
Figure 1:
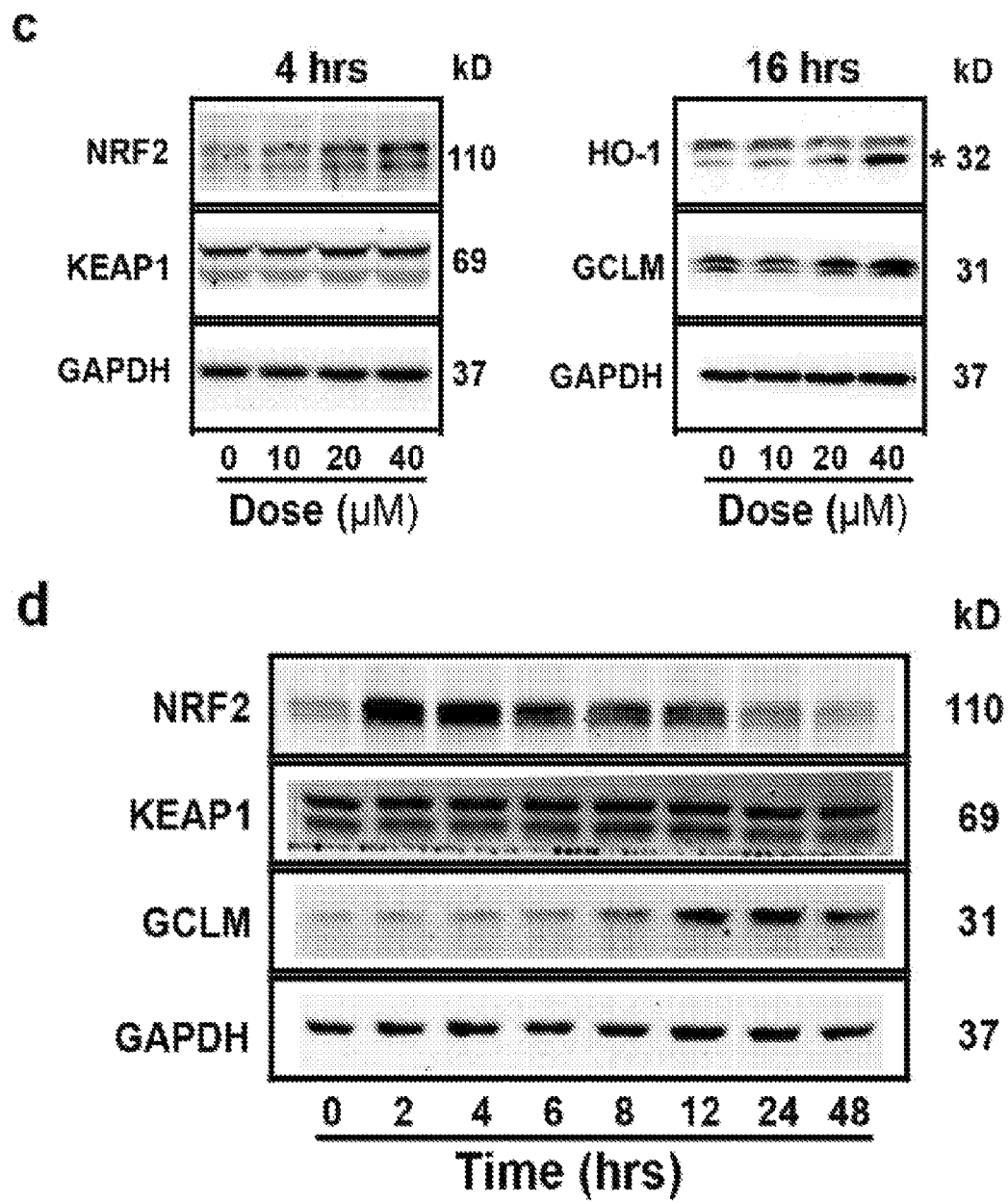
Figure 1:
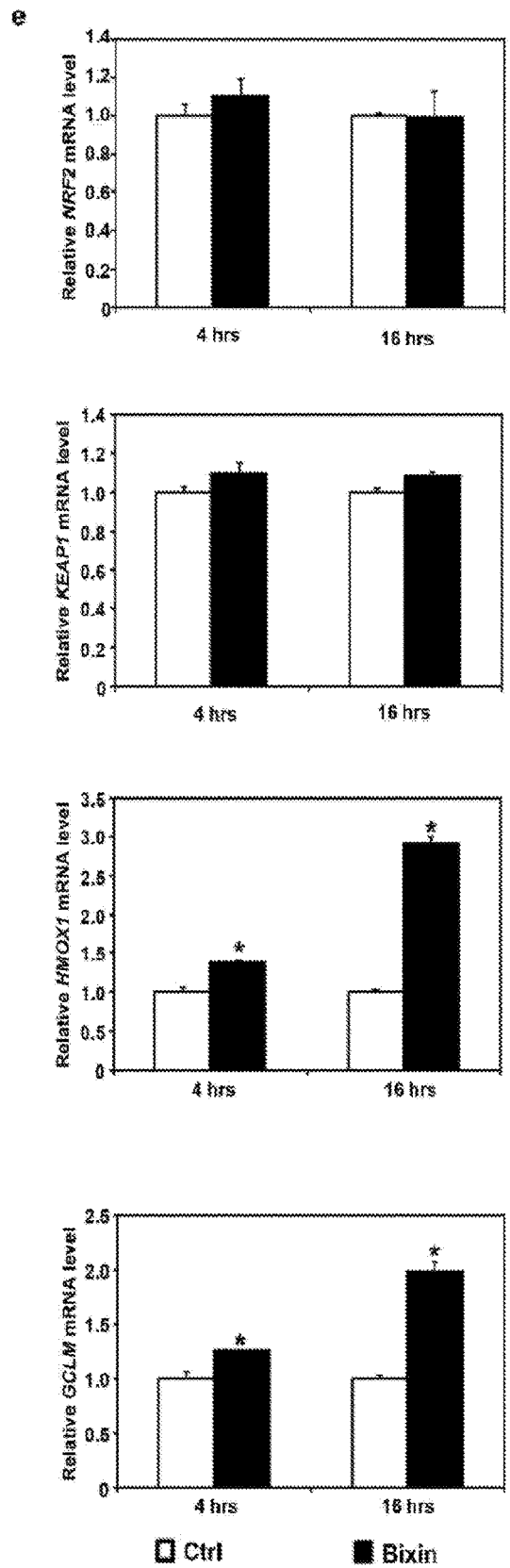

"Subject," "individual," "host," "animal," and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

As used herein, the terms "administration" and "administering" refer to the act of giving a drug, prodrug, or other agent, or therapeutic treatment (e.g., bixin) to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., multiple NRF2 activating agents (e.g., bixin or derivatives, variants, or mimetics thereof), or bixin and another therapeutic agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

"Treatment," as used herein, covers any administration or application of a therapeutic for disease in a mammal, including a human, and includes inhibiting the disease, arresting its development, or relieving the disease, for example, by causing regression, or restoring or repairing a lost, missing, or defective function; or stimulating an inefficient process.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

The term "derivative" of a compound, as used herein, refers to a chemically modified compound wherein the chemical modification takes place either at a functional group of the compound or backbone.

The term "diagnosed," as used herein, refers to the recognition of a disease by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., lung injury). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

Provided herein are compositions and methods for treating and preventing lung injury (e.g. ventilation induced lung injury). In particular, the invention relates to compositions and methods for treating and preventing airway disease by activating the NRF2 pathway.

The main cellular cytoprotective response is orchestrated by the transcription factor NRF2 (nuclear factor-E2-related factor 2), which controls the expression of numerous antioxidant, anti-inflammatory, and pro-survival genes that contain antioxidant response elements (ARE) in their promoters (Jaramillo, M. C. & Zhang, D. D. The emerging role of the Nrf2-Keap1 signaling pathway in cancer. Genes Dev 27, 2179-91 (2013); Kensler, T. W., Wakabayashi, N. & Biswal, S. Cell survival responses to environmental stresses via the Keap1-Nrf2-ARE pathway. Annu Rev Pharmacol Toxicol 47, 89-116 (2007)). Typically, NRF2 is ubiquitously expressed and maintained at low levels but is activated quickly in response to various cellular stresses, including mechanical stress (Papaiahgari, S. et al. Genetic and pharmacologic evidence links oxidative stress to ventilator-induced lung injury in mice. Am J Respir Crit Care Med 176, 1222-35 (2007); Mirzapoiazova, T. et al. Non-muscle myosin light chain kinase isoform is a viable molecular target in acute inflammatory lung injury. Am J Respir Cell Mol Biol 44, 40-52 (2011)). Pre-activation of NRF2 facilitates an adaptive response that protects against various types of stresses encountered subsequently. The use of natural compounds to activate NRF2 signaling has proved to be a feasible chemopreventive strategy, as demonstrated in various preclinical studies (Shen, T. et al. Plant extracts of the family Lauraceae: a potential resource for chemopreventive agents that activate the nuclear factor-erythroid 2-related factor 2/antioxidant response element pathway. Planta Med 80, 426-34 (2014); Tao, S., Justiniano, R., Zhang, D. D. & Wondrak, G. T. The Nrf2-inducers tanshinone I and dihydrotanshinone protect human skin cells and reconstructed human skin against solar simulated UV. Redox Biol 1, 532-41 (2013); Zheng, Y. et al. Sulforaphane prevents pulmonary damage in response to inhaled arsenic by activating the Nrf2-defense response. Toxicol Appl Pharmacol 265, 292-9 (2012)). Many natural compounds that are used in traditional medicine for their antioxidant and anti-inflammatory properties have been shown to be Nrf2 inducers that elicit their effect through NRF2 activation (Shen, T. et al. Plant extracts of the family Lauraceae: a potential resource for chemopreventive agents that activate the nuclear factor-erythroid 2-related factor 2/antioxidant response element pathway. Planta Med 80, 426-34 (2014); Surh, Y. J. Cancer chemoprevention with dietary phytochemicals. Nat Rev Cancer 3, 768-80 (2003); Lau, A., Whitman, S. A., Jaramillo, M. C. & Zhang, D. D. Arsenic-mediated activation of the Nrf2-Keap1 antioxidant pathway. J Biochem Mol Toxicol 27, 99-105 (2013)). Hence, numerous studies have demonstrated the protective effect of NRF2 against pathologic conditions that present oxidative stress and inflammation (Giuliano, G., Rosati, C. & Bramley, P. M. To dye or not to dye: biochemistry of annatto unveiled. Trends Biotechnol 21, 513-6 (2003); Jiang, T. et al. Nrf2 suppresses lupus nephritis through inhibition of oxidative injury and the NF-kappaB-mediated inflammatory response. Kidney Int (2013); Meakin, P. J. et al. Susceptibility of Nrf2-null mice to steatohepatitis and cirrhosis upon consumption of a high-fat diet is associated with oxidative stress, perturbation of the unfolded protein response, and disturbance in the expression of metabolic enzymes but not with insulin resistance. Mol Cell Biol 34, 3305-20 (2014); Cho, H. Y., Reddy, S. P., Yamamoto, M. & Kleeberger, S. R. The transcription factor NRF2 protects against pulmonary fibrosis. FASEB J 18, 1258-60 (2004)). Mechanisms of NRF2 activation by chemopreventive compounds have been studied in detail. Activation of NRF2 in response to chemopreventive compounds or a change in the intracellular redox status is controlled by KEAP1, a substrate adaptor protein of E3-ubiquitin ligase that binds to NRF2 and negatively regulates it (Kobayashi, A. et al. Oxidative stress sensor Keap1 functions as an adaptor for Cul3-based E3 ligase to regulate proteasomal degradation of Nrf2. Mol Cell Biol 24, 7130-9 (2004); Zhang, D. D., Lo, S. C., Cross, J. V., Templeton, D. J. & Hannink, M. Keap1 is a redox-regulated substrate adaptor protein for a Cul3-dependent ubiquitin ligase complex. Mol Cell Biol 24, 10941-53 (2004)). Critical cysteine residues in KEAP1 get oxidized by ROS or modified by electrophilic compounds, which then alters its interaction with NRF2 and prevents its degradation (Zhang, D. D. & Hannink, M. Distinct cysteine residues in Keap1 are required for Keap1-dependent ubiquitination of Nrf2 and for stabilization of Nrf2 by chemopreventive agents and oxidative stress. Mol Cell Biol 23, 8137-51 (2003); Dinkova-Kostova, A. T. et al. Direct evidence that sulfhydryl groups of Keap1 are the sensors regulating induction of phase 2 enzymes that protect against carcinogens and oxidants. Proc Natl Acad Sci USA 99, 11908-13 (2002)). Chemopreventive compounds such as sulforaphane (SF) and tert-butylhydroquinone (tBHQ) induce NRF2 in a KEAP1 cysteine-151 (C151)-dependent manner. In contrast, carcinogenic arsenic upregulates NRF2 through p62-autophagy blockage (Zhang, D. D. & Hannink, M. Distinct cysteine residues in Keap1 are required for Keap1-dependent ubiquitination of Nrf2 and for stabilization of Nrf2 by chemopreventive agents and oxidative stress. Mol Cell Biol 23, 8137-51 (2003); Wang, X. J. et al. Activation of Nrf2 by arsenite and monomethylarsonous acid is independent of Keap1-C151: enhanced Keap1-Cul3 interaction. Toxicol Appl Pharmacol 230, 383-9 (2008)).

Bixin is a carotenoid extracted from the seeds of *Bixa orellana* (annatto, or 'achiote' in Mexico) used as an FDA-approved food colorant and additive, as well as cosmetic and textile colorant (Giuliano, G., Rosati, C. & Bramley, P. M. To dye or not to dye: biochemistry of annatto unveiled. Trends Biotechnol 21, 513-6 (2003)). Traditionally, it has been used in Mexico and South America to treat infectious and inflammatory diseases of the skin, prostate, gastrointestinal tract, and chest pain (Vilar Dde, A. et al. Traditional uses, chemical constituents, and biological activities of *Bixa orellana* L.: a review. ScientificWorldJournal 2014, 857292 (2014); Tibodeau, J. D., Isham, C. R. & Bible, K. C. Annatto constituent cis-bixin has selective antimyeloma effects mediated by oxidative stress and associated with inhibition of thioredoxin and thioredoxin reductase. Antioxid Redox Signal 13, 987-97 (2010)). Previous in vitro biochemical assays demonstrated that bixin was able to quench singlet oxygen, a ROS implicated in oxidative lung injury (Di Mascio, P., Devasagayam, T. P., Kaiser, S. & Sies, H. Carotenoids, tocopherols and thiols as biological singlet molecular oxygen quenchers. Biochem Soc Trans 18, 1054-6 (1990); Chiste, R. C. et al. In vitro scavenging capacity of annatto seed extracts against reactive oxygen and nitrogen species. Food Chem 127, 419-26 (2011)). Consistent with its antioxidant properties, other studies demonstrate that bixin prevents oxidative DNA damage and lipid peroxidation. Bixin also protects against cisplatin-induced clastogenicity and carbon tetrachloride hepatotoxicity (Dos Santos, G. C. et al. Protective effect of bixin on cisplatin-induced genotoxicity in PC12 cells. Food Chem Toxicol 50, 335-40 (2012); Moreira, P. R. et al. Protective effect of bixin on carbon tetrachloride-induced hepatotoxicity in rats. Biol Res 47, 49 (2014); Silva, C. R., Antunes, L. M. & Bianchi, M. L. Antioxidant action of bixin against cisplatin-induced chromosome aberrations and lipid peroxidation in rats. Pharmacol Res 43, 561-6 (2001)). Currently, there is no epidemiological evidence of carcinogenicity or acute toxicity associated to ingestion or occupational exposure to bixin, and asides from rare cases of reported allergies to bixin ingestion, this compound has been proven to be safe for human administration (Stohs, S. J. Safety and efficacy of *Bixa orellana* (achiote, annatto) leaf extracts. Phytother Res 28, 956-60 (2014); Auttachoat, W., Germolec, D. R., Smith, M. J., White, K. L., Jr. & Guo, T. L. Contact sensitizing potential of annatto extract and its two primary color components, cis-bixin and norbixin, in female BALB/c mice. Food Chem Toxicol 49, 2638-44 (2011)).

Figure 2:
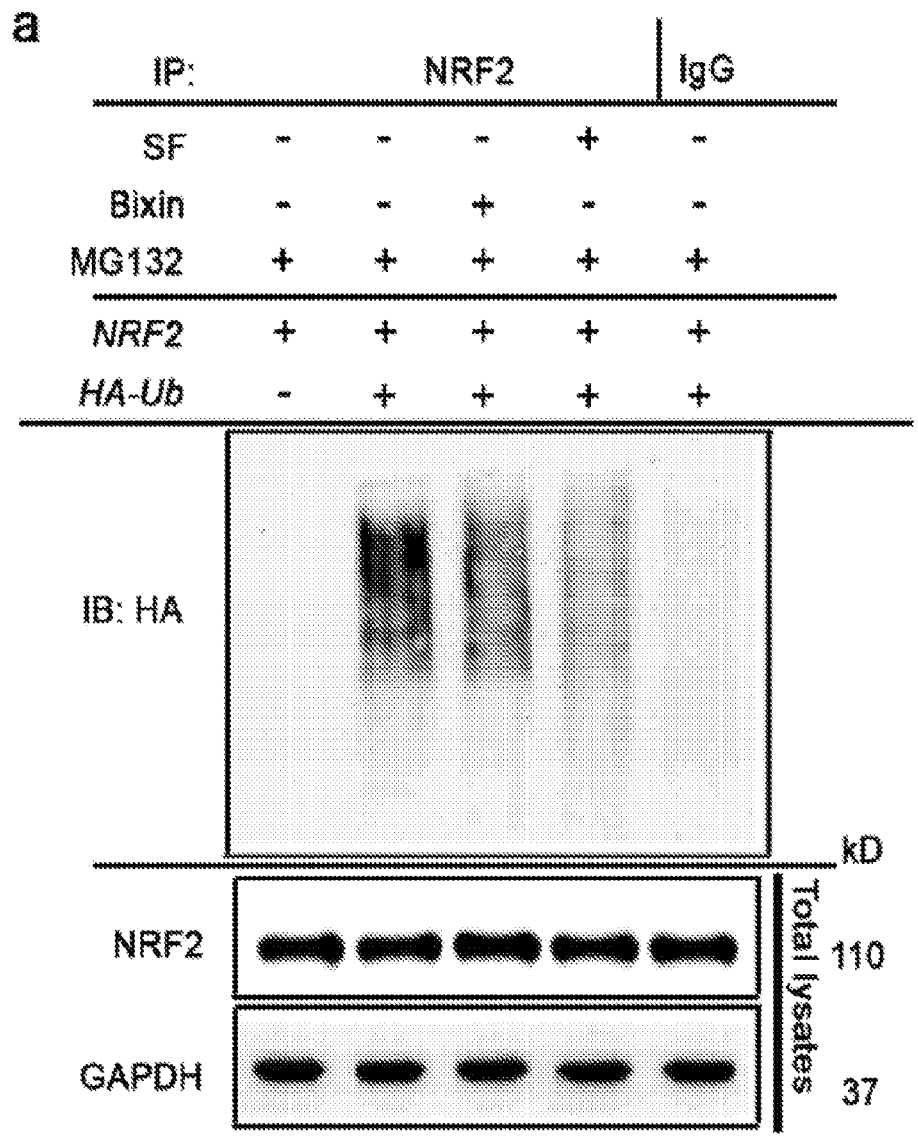
FIG. 2 shows that bixin activates the NRF2 signaling pathway by decreasing NRF2 ubiquitination and increasing NRF2 protein stability in a Keap1-C151-dependent manner. (a) H1299 cells were cotransfected with plasmids encoding the indicated proteins; 24 h later the cells were treated with either SF (5 µM) or bixin (40 µM) along with MG132 (10 µM) for 4 h. (b) H1299 cells were transfected with siRNA and 24 h later were transfected with plasmids encoding the indicated KEAP1 proteins. (c) H1299 cells cotransfected with the plasmids expressing either wild type Keap1 (KEAP1-WT) or C151 mutated Keap1 (KEAP1-C151S) along with mGst-ARE firefly luciferase and *Renilla* luciferase reporters were left untreated or treated with the indicated compounds for 16 h. (d) H1299 cells were either left untreated or treated with bixin (40 µM) for 4 h.
Figure 2:
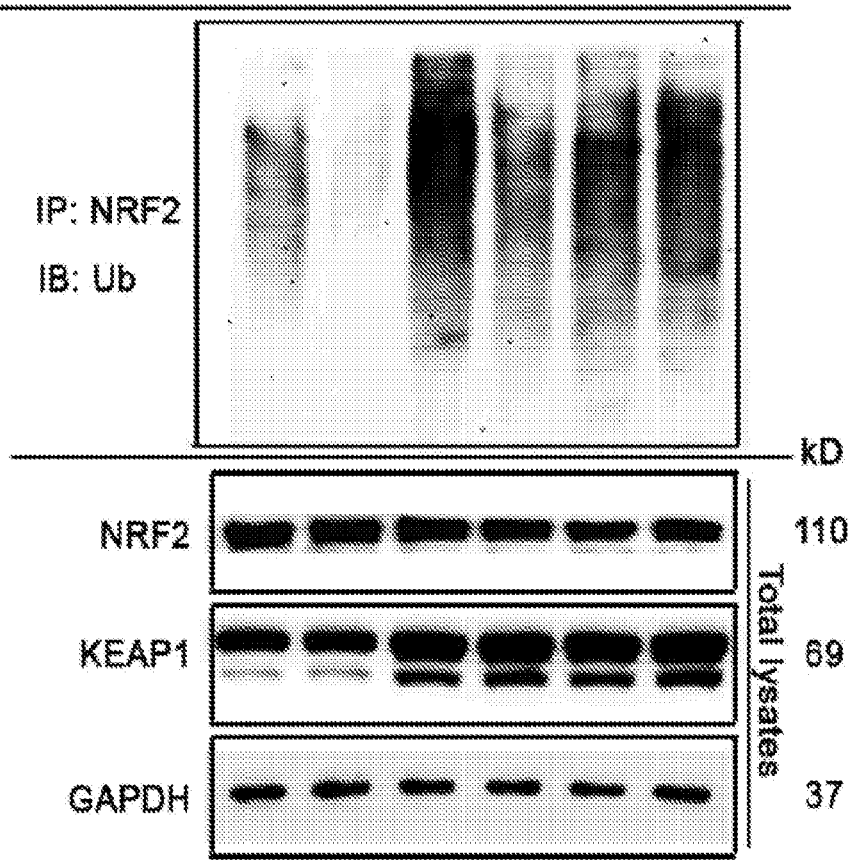
Figure 2:
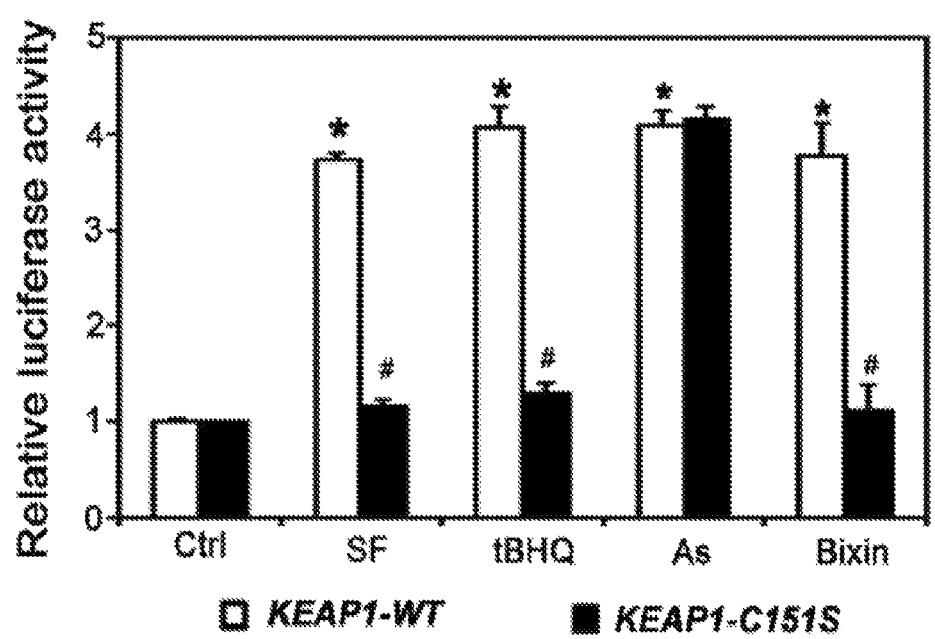
Figure 2:
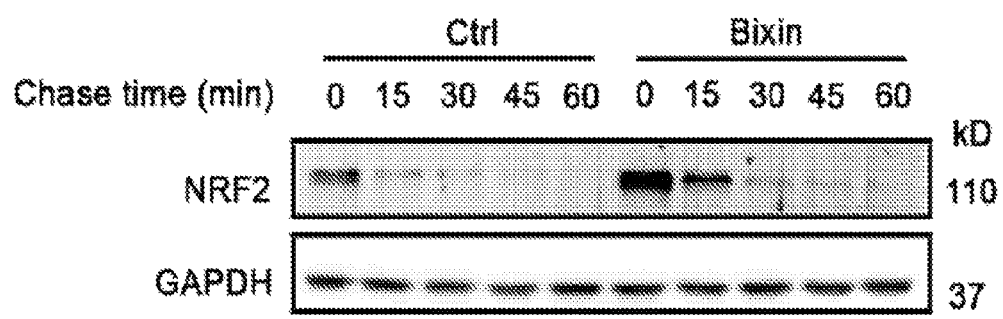
Figure 2:
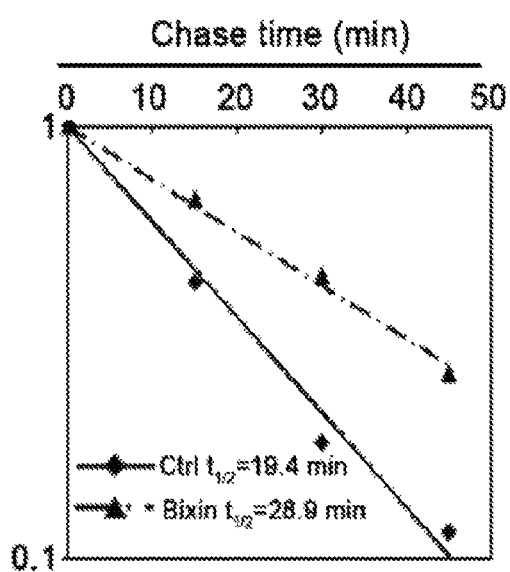
Figure 3:
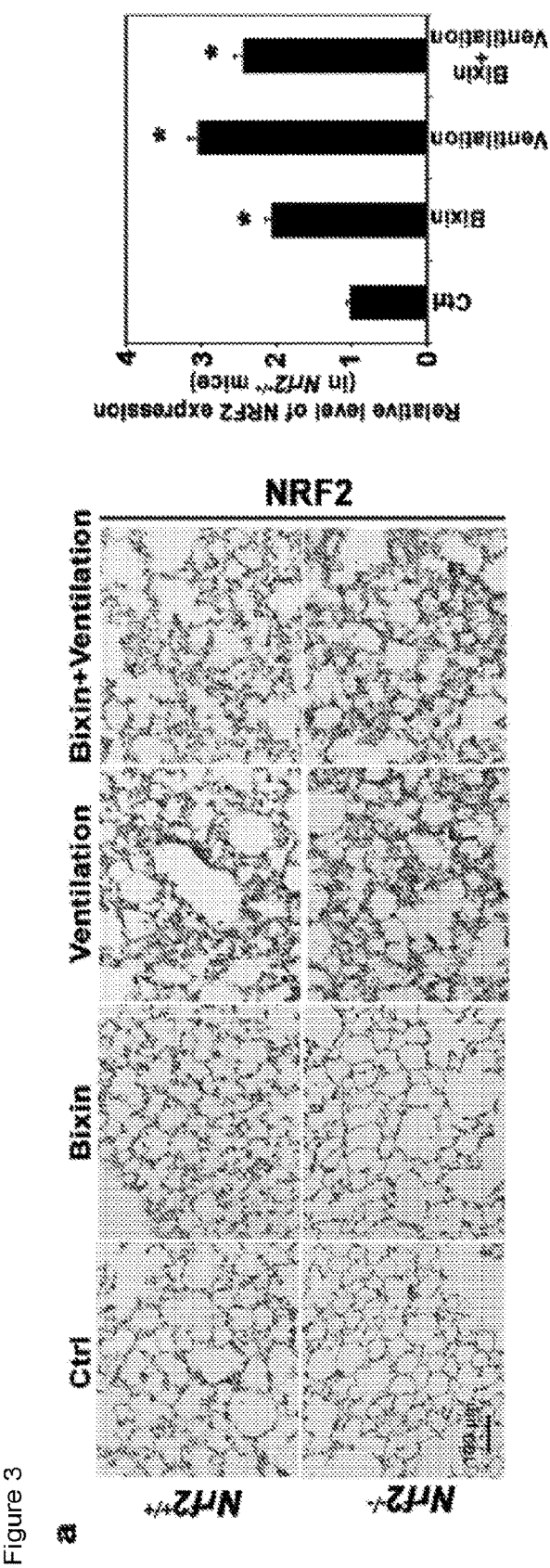
FIG. 3 shows that bixin activates the NRF2 signaling pathway and suppresses the NF-κB inflammatory response in the lungs of Nrf2$^{+/+}$ mice. IHC staining of (a) NRF2, (b) HMOX1, and (c) GCLM of lung tissue sections from Nrf2$^{+/+}$ and Nrf2$^{-/-}$ mice (n=6, a representative image of the lung tissue from each group is shown to the left).
Figure 3:
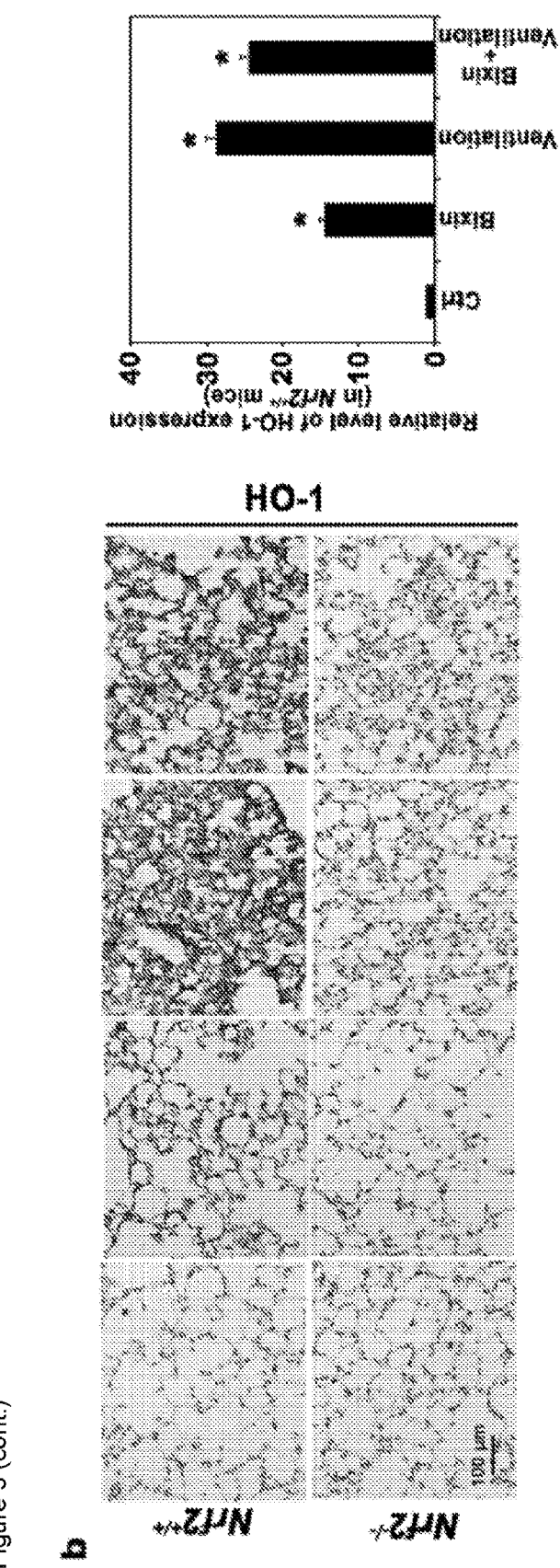
Figure 3:
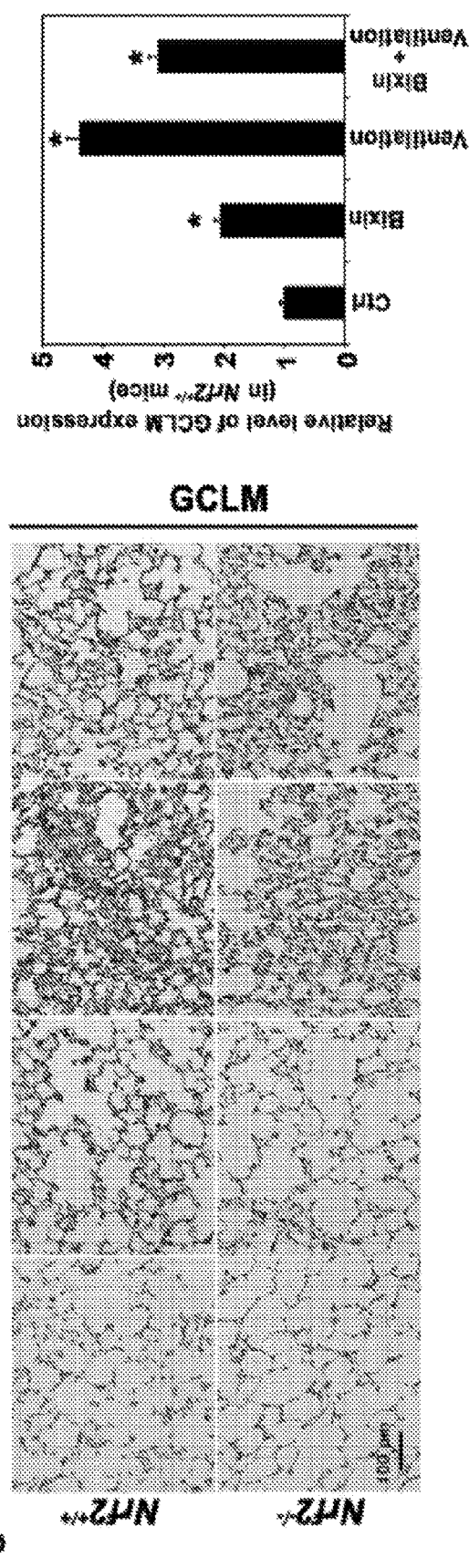
Figure 4:
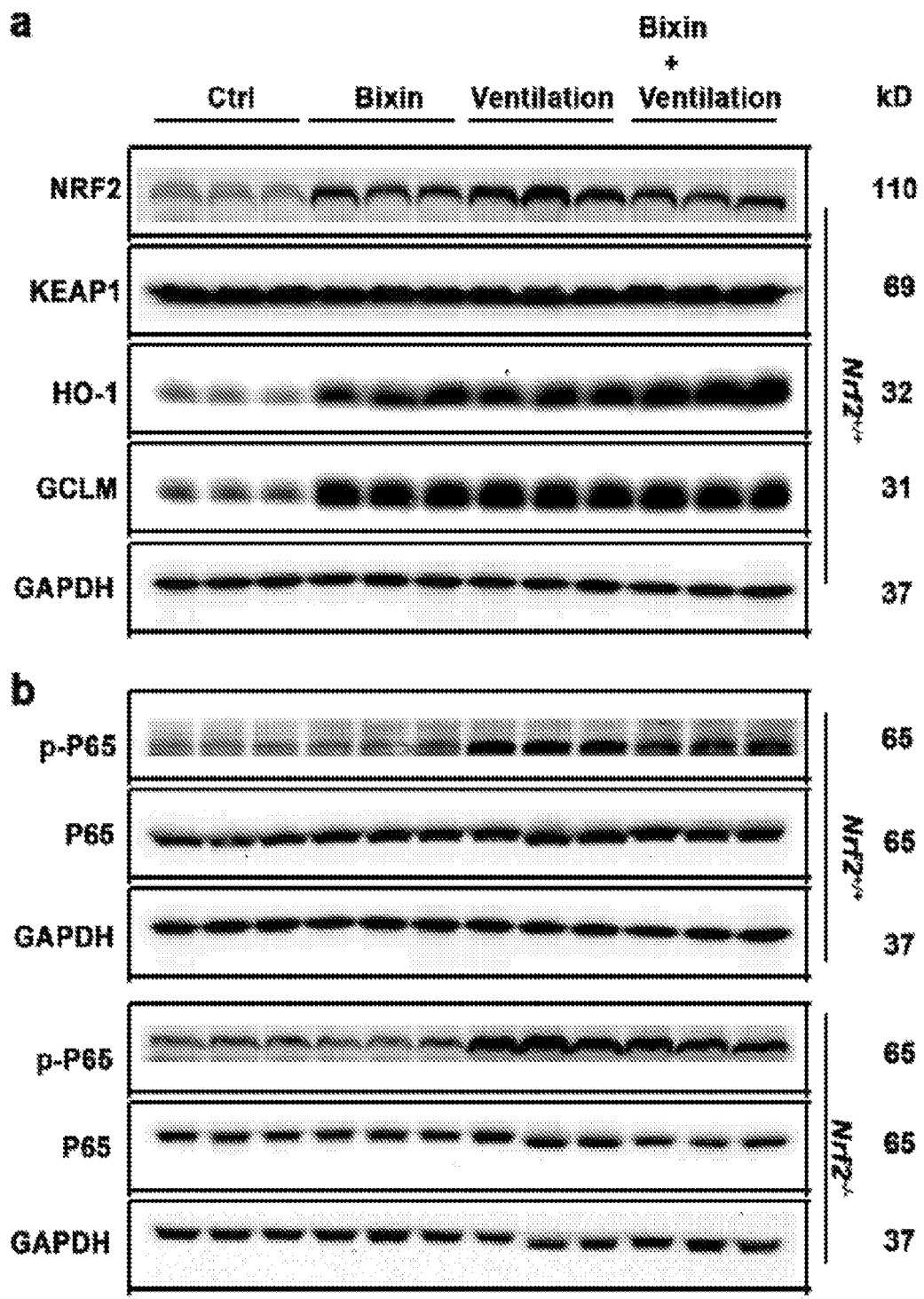
FIG. 4 shows that bixin attenuates ventilation-induced inflammation by inducing the NRF2 signaling pathway and decreasing P65 phosphorylation in the lungs from Nrf2$^{+/+}$ but not Nrf2$^{-/-}$ mice. Lung tissue lysates from Nrf2$^{+/+}$ mice and Nrf2$^{-/-}$ mice (n=3) were subjected to immunoblot analysis with (a) NRF2 pathway and (b) NF-κB pathway (P65, p-P65) antibodies. The mRNA levels of (c) Nrf2, (d) Keap1, (e) Hmox1, and (f) Gclm were measured with RT-PCR assay.
Figure 4:
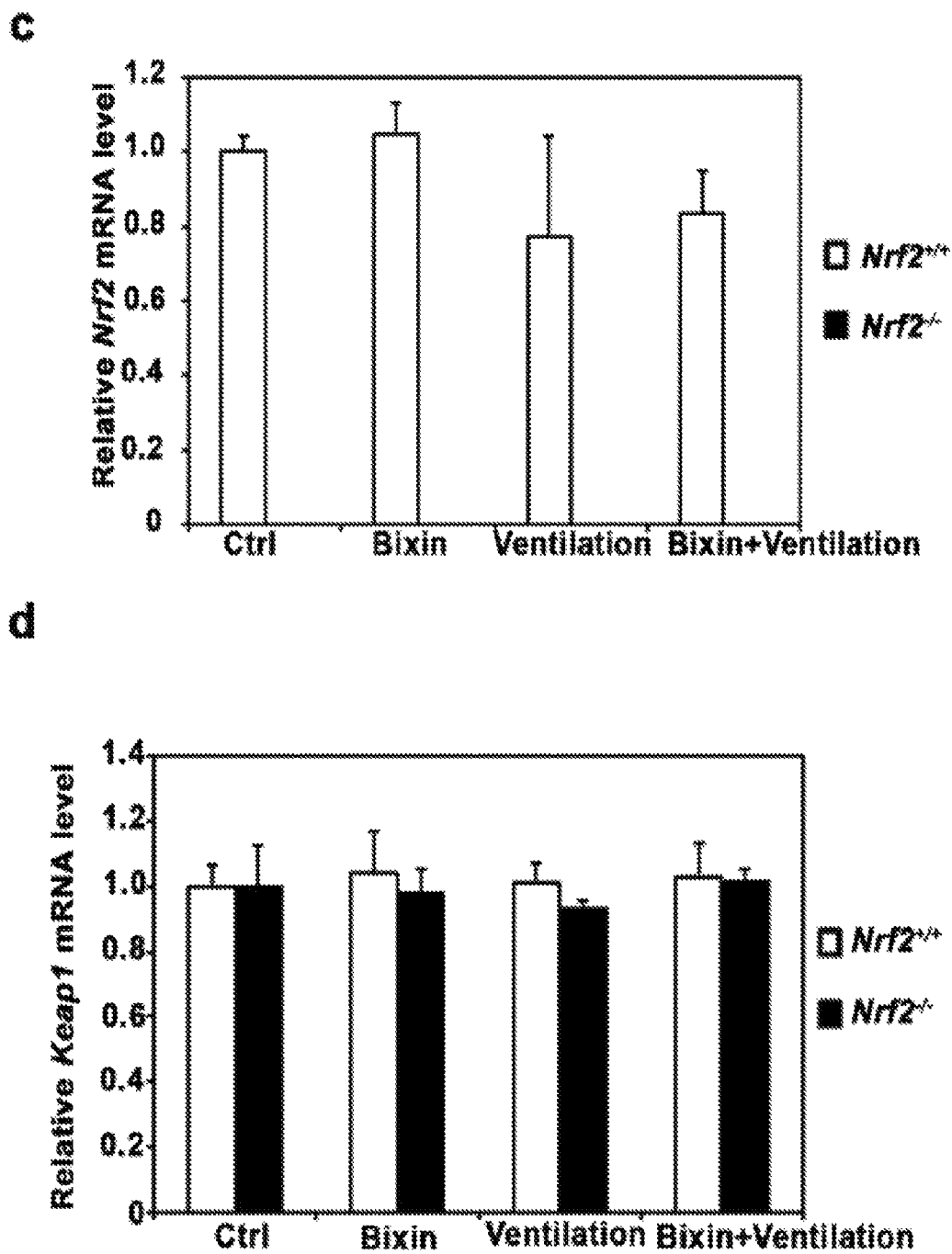
Figure 4:
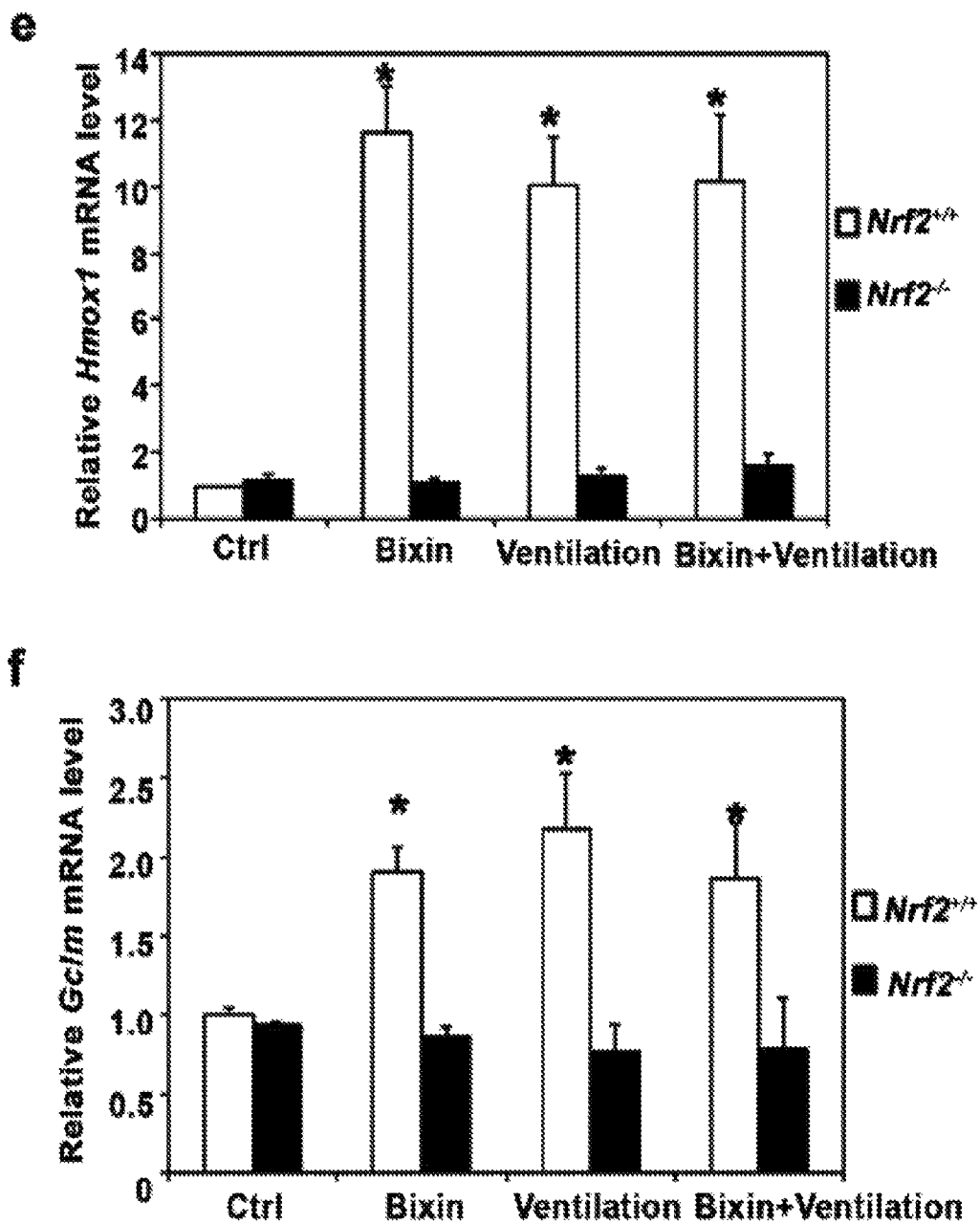
Figure 5:
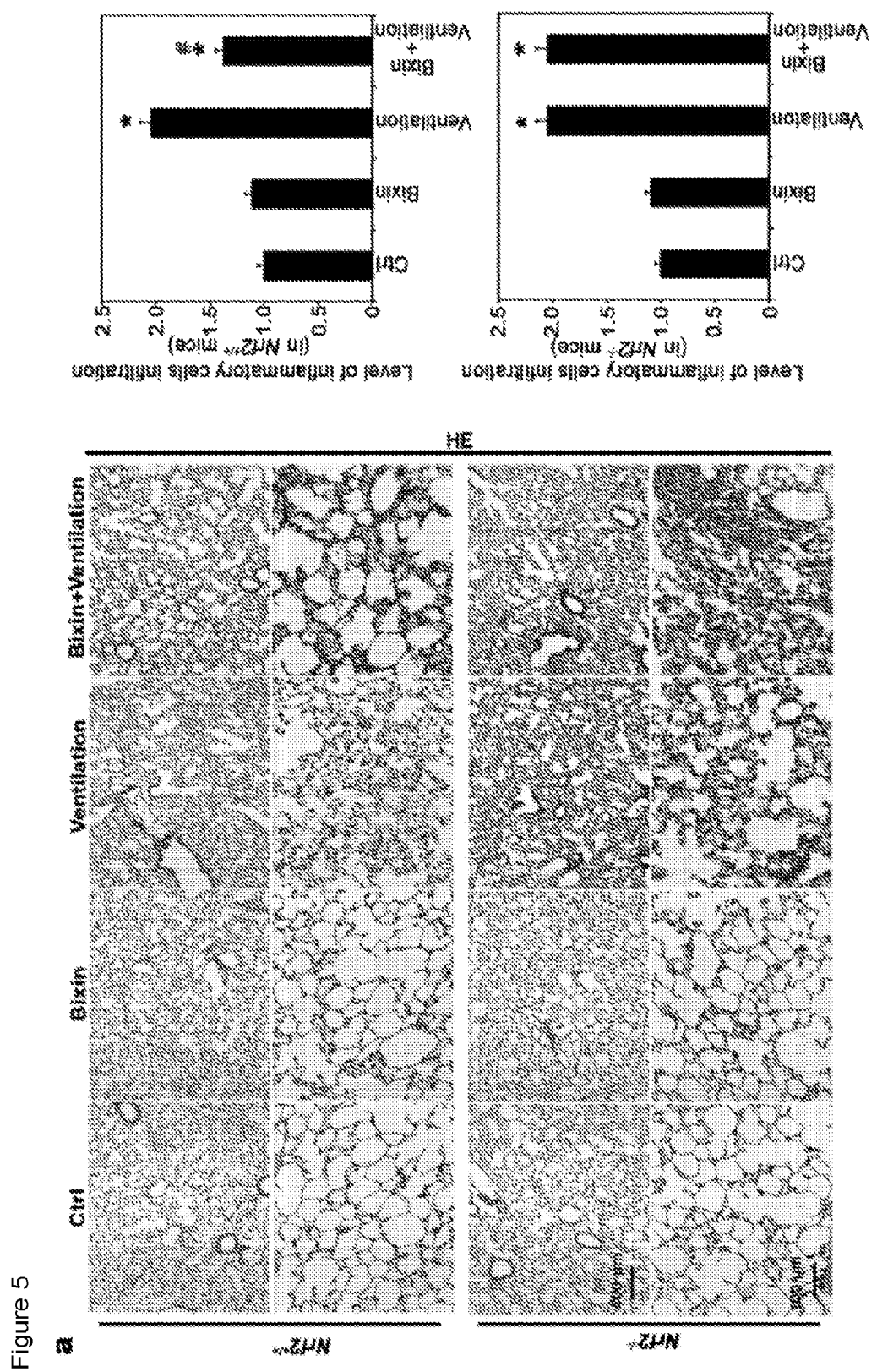
FIG. 5 shows that bixin decreases ventilation-induced inflammation and oxidative DNA damage in the lungs of Nrf2$^{+/+}$ but not Nrf2$^{-/-}$ mice. (a) HE staining and (b) IHC of 8-oxo-dG of lung tissue sections from Nrf2$^{+/+}$ and Nrf2$^{-/-}$ mice (n=6), a representative image (left, amplification: 100×, top, and 400×, bottom) of the lung tissues from each group is shown). Scale bar for 100×: 400 µm; 400×: 100 µm.
Figure 5:
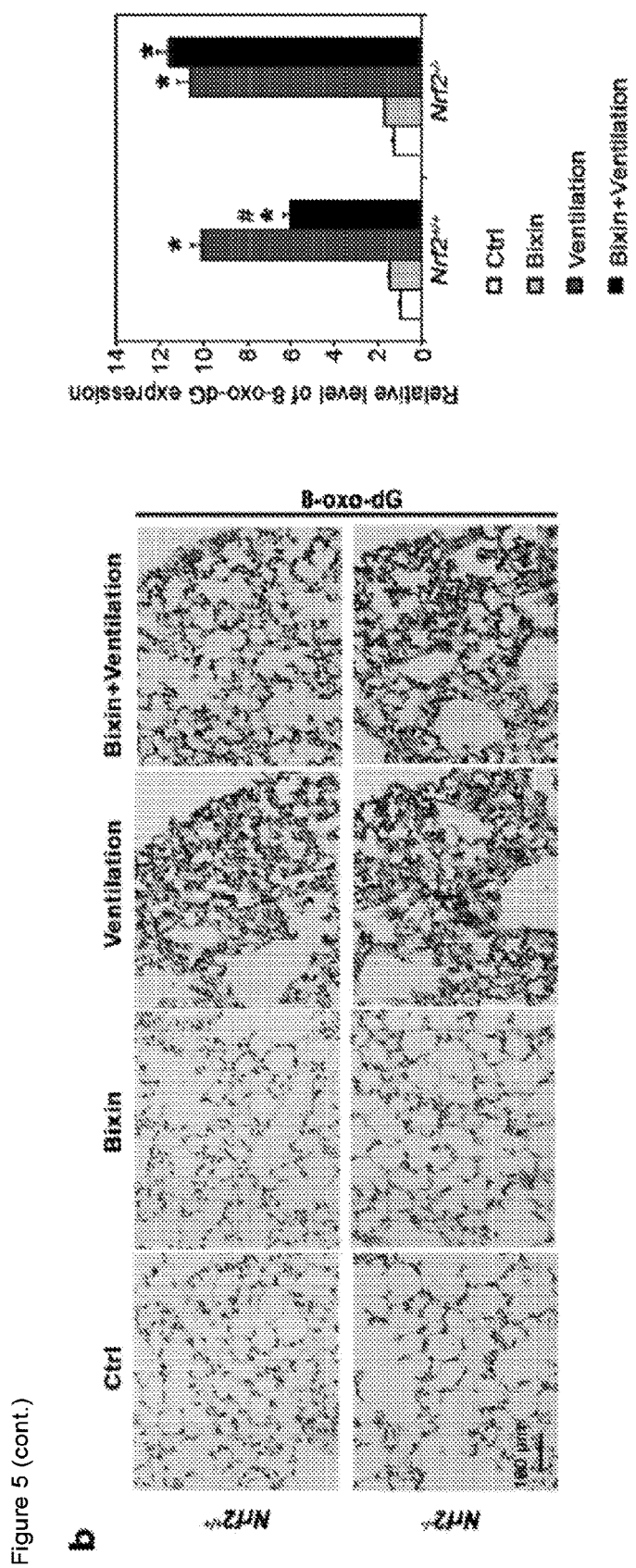
Figure 6:
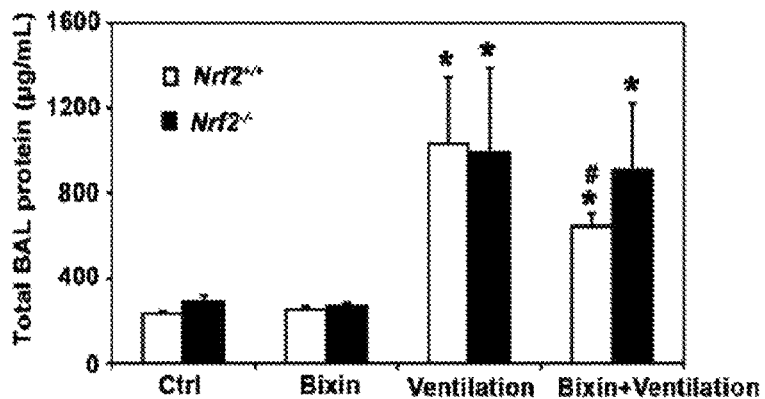
FIG. 6 shows that bixin attenuates ventilation-induced inflammation in the lungs of Nrf2$^{+/+}$ but not Nrf2$^{-/-}$ mice. (a) Total BAL protein, and (b) total BAL cell number were measured for Nrf2$^{+/+}$ and Nrf2$^{-/-}$ mice. (c) Cell differential analysis was performed on the BAL cells from each mouse. At least 200 cells were counted per sample and the ratio of neutrophils to total cells was plotted. The amount of (d) IL6 and (e) TNFα in the BAL fluid was measured by ELISA (n=6).
Figure 6:
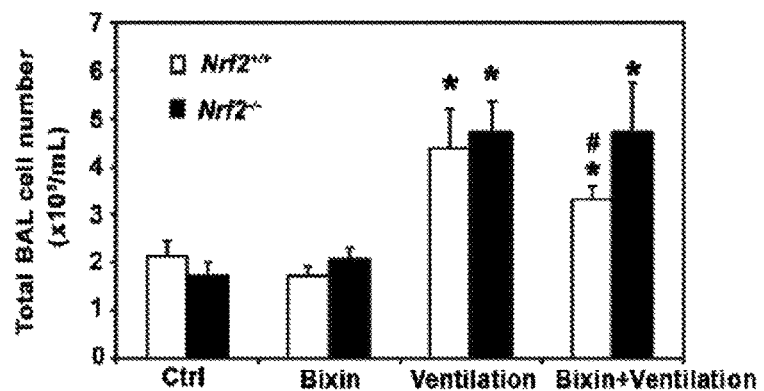
Figure 6:
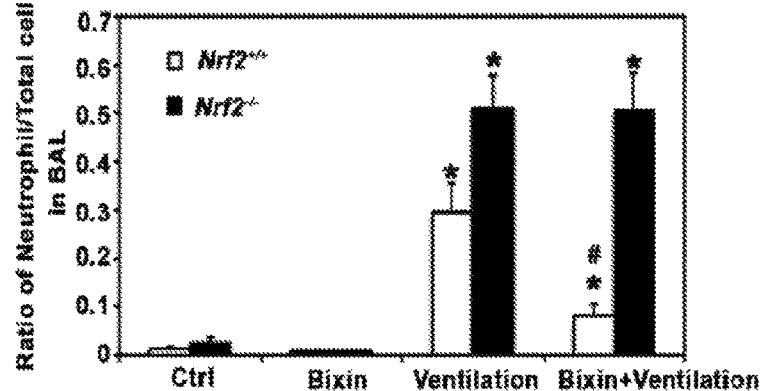
Figure 6:
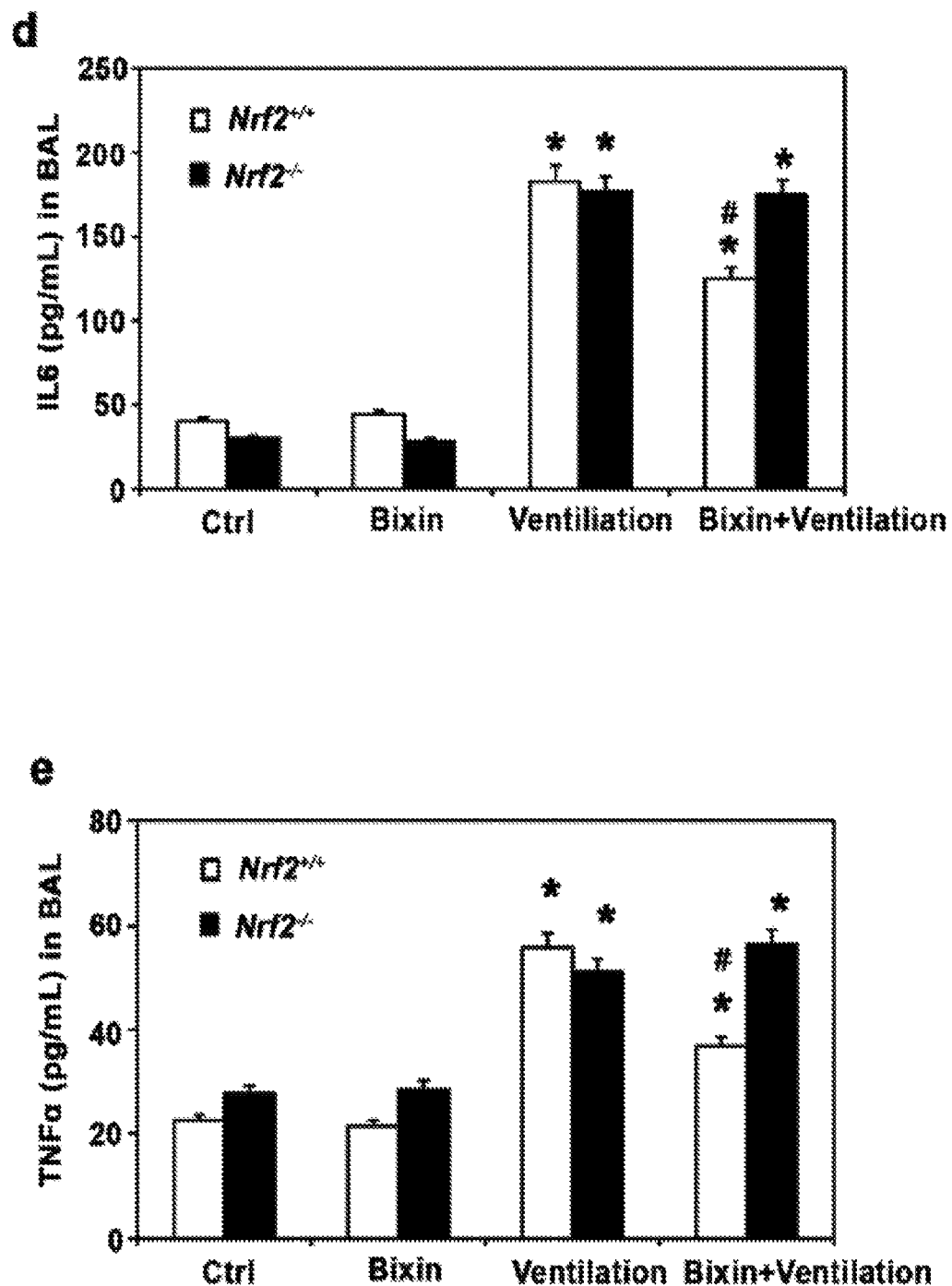

Experiments described herein identified bixin as a novel canonical NRF2 inducer, indicating that the previously defined antioxidant and anti-inflammatory properties of bixin may be derived from activation of the NRF2-mediated response, rather than acting as a direct ROS scavenger as previously reported. Bixin was found to activate the NRF2 signaling pathway in lung epithelial cells and in the lungs of mice through IP injection. The protective effects of bixin were investigated in a murine VILI model. Bixin protects against VILI by suppression of inflammatory mediators, reduction in alveolar capillary leakage, and protection against DNA oxidative damage in an NRF2-dependant manner. These results indicate that pharmacological activation of NRF2 by bixin pretreatment may ameliorate the lung damage induced by MV VILI is a negative side effect of MV that contributes to patient morbidity and mortality despite being the most effective therapy against respiratory deficiencies. In the pathology of VILI, two major events have been identified: volutrauma (damage induced by high respiratory volumes) and biotrauma (damage induced by the mechanical stretching of the airways that produces an inflammatory response) (Kuchnicka, K. & Maciejewski, D. Ventilator-associated lung injury. Anaesthesiol Intensive Ther 45, 164-70 (2013)). The first event can be partially reversed by using low tidal volumes for ventilation. However, there are currently no treatments to decrease the biotrauma. Experiments described herein demonstrated the use of NRF2 activators in decreasing VILI using the canonical NRF2 activator bixin. First, bixin was identified as an NRF2 pathway activator in vitro (FIG. 1). Bixin works in a KEAP1-C151-dependent fashion to prevent NRF2 ubiquitination and prolong its half-life, and is therefore defined as a canonical NRF2 activator (FIG. 2). Thus, it is contemplated that the previously reported antioxidant activity of bixin is actually through NRF2 activation. Next, the in vivo protective effects of bixin in ameliorating VILI were investigated. Mechanical ventilation itself induced NRF2, HO-1 and GCLM. However, it also elicited a severe inflammatory response (as measured by p-P65 protein levels, total BAL protein, increased BAL cells and neutrophils, and increased levels of inflammatory cytokines) and oxidative stress (as measured by DNA oxidative damage) (FIGS. 3-6). Bixin induces the expression of NRF2 and its downstream targets in lung tissues of Nrf2+/+ mice (FIG. 3). Bixin pretreatment restored normal lung morphology and alleviated MV-induced inflammation and oxidative stress; these effects are dependent on NRF2 signaling since Nrf2−/− mice did not benefit from bixin pretreatment (FIGS. 3-6).

VILI upregulates the NRF2 response in lung tissues (Papaiahgari, S. et al. Genetic and pharmacologic evidence links oxidative stress to ventilator-induced lung injury in mice. Am J Respir Crit Care Med 176, 1222-35 (2007); Mirzapoiazova, T. et al. Non-muscle myosin light chain kinase isoform is a viable molecular target in acute inflammatory lung injury. Am J Respir Cell Mol Biol 44, 40-52 (2011)) and that genetic ablation of Nrf2 increases inflammation and oxidative injuries in mice. Papaiahgari et al. found that VILI produced high alveolo-endothelial permeability (total BAL protein) in both Nrf2+/+ and Nrf2−/− mice to a similar degree (Papaiahgari, S. et al. Genetic and pharmacologic evidence links oxidative stress to ventilator-induced lung injury in mice. Am J Respir Crit Care Med 176, 1222-35 (2007)). They also reported that Nrf2−/− mice had a higher neutrophil infiltration to the lungs than their wild-type counterparts. Both observations are consistent with this study. Another study found that sodium sulfide protects against VILI by upregulating NQO1 and GPX248, which are involved in the restoration of redox balance. Additionally, hyperoxia causes acute lung injury (ALI), which resembles VILI in that it causes lung hyperpermeability and inflammation by induction of NF-κB and pro-inflammatory cytokine release (Liu, Y. Y. et al. Role for nuclear factor-kappaB in augmented lung injury because of interaction between hyperoxia and high stretch ventilation. Transl Res 154, 228-40 (2009)). Another study has identified that conditional deletion of NRF2 in lung epithelial cells causes greater lung injury and prolonged inflammation, as well as increased alveolar permeability, under hyperoxic conditions (Reddy, N. M., Potteti, H. R., Mariani, T. J., Biswal, S. & Reddy, S. P. Conditional deletion of Nrf2 in airway epithelium exacerbates acute lung injury and impairs the resolution of inflammation. Am J Respir Cell Mol Biol 45, 1161-8 (2011)). These studies support the hypothesis that hyperoxia is an effect of MV and that NRF2 activation protects the lungs from VILI and ALI by inducing the transcription of antioxidant proteins and by downregulating NF-κB signaling (Cho, H. Y. & Kleeberger, S. R. Nrf2 protects against airway disorders. Toxicol Appl Pharmacol 244, 43-56 (2010); Chen, H. et al. NFkB and Nrf2 in esophageal epithelial barrier function. Tissue Barriers 1, e27463 (2013)).

Accordingly, provided herein are method of treating and preventing VILI using NRF2 activation. Since MV is a procedure that can be anticipated, in some embodiments, preventive therapy that induces NRF2 is started before the procedure is initiated to decrease its negative side effects (Dos Santos, C. C. & Slutsky, A. S. Invited review: mechanisms of ventilator-induced lung injury: a perspective. J Appl Physiol (1985) 89, 1645-55 (2000)). Although the use of direct antioxidants, like N-acetyl cysteine (NAC), has some degree of beneficial effects (Papaiahgari, S. et al. Genetic and pharmacologic evidence links oxidative stress to ventilator-induced lung injury in mice. Am J Respir Crit Care Med 176, 1222-35 (2007)), it is contemplated that activating the body's own defensive responses through upregulation of the NRF2 pathway in combination with low tidal ventilator strategies results in greater benefits for the patients. The use of carotenoids in chemopreventive interventions has been extensively documented although the results have proven little to no effect, probably due to their limited action as ROS quenchers (Bertram, J. S. et al. Diverse carotenoids protect against chemically induced neoplastic transformation. Carcinogenesis 12, 671-8 (1991); Roehrs, M. et al. Bixin and norbixin have opposite effects on glycemia, lipidemia, and oxidative stress in streptozotocin-induced diabetic rats. Int J Endocrinol 2014, 839095 (2014); Zhang, L. X., Cooney, R. V. & Bertram, J. S. Carotenoids enhance gap junctional communication and inhibit lipid peroxidation in C3H/10T1/2 cells: relationship to their cancer chemopreventive action. Carcinogenesis 12, 2109-14 (1991); Kaulmann, A. & Bohn, T. Carotenoids, inflammation, and oxidative stress—implications of cellular signaling pathways and relation to chronic disease prevention. Nutr Res 34, 907-29 (2014); Tanaka, T., Shnimizu, M. & Moriwaki, H. Cancer Chemoprevention by Carotenoids. Molecules 17, 3202-3242 (2012).). The results described herein indicate that bixin administration before MV improves the patients' outcomes due to not only its quenching properties but also to its ability to upregulate the antioxidant and anti-inflammatory responses. In humans, the maximum bixin concentration in blood plasma is detected at 2 h post-ingestion (Levy, L. W., Regalado, E., Navarrete, S. & Watkins, R. H. Bixin and norbixin in human plasma: determination and study of the absorption of a single dose of Annatto food color. Analyst 122, 977-80 (1997)), so bixin administration is a good option even for patients receiving emergency MV. A major concern in the administration of carotenoids is that at high doses they have pro-oxidant effects, however the bixin doses used in the in vivo studies did not elicit any cytotoxicity or generate oxidative DNA damage while inducing a robust NRF2 response. The results described herein demonstate that bixin alleviates VILI by induction of NRF2 to decrease inflammation and oxidative damage. Therefore, this study indicates that pharmacological activation of NRF2 with natural compounds such as bixin or pharmaceutical agents is beneficial to patients who will receive or are receiving MV treatment. It is also contemplated that the beneficial effects identified in the lung might also be present in other vital organs (like kidneys) affected by the negative side effects of MV, since IP injection of NRF2 inducers is able to activate NRF2 in many organs tested (data not shown).

Accordingly, provided herein are compositions and methods for treating and preventing VILI using agents that activate the NRF2 pathway. In some embodiment, the agent is bixin. However, the present invention is not limited to bixin or derivatives or mimetics thereof. Any agent that activates NRF2 signaling and has the desired outcome (e.g., treatment and/or prevention of VILI is specifically contemplated.

In some embodiments, two or more agents (e.g., two or more agents that activate NRF2 signaling or one agent that activates NRF2 signaling in combination with a second agent (e.g., antioxidant or carotenoid)) are utilized. Multiple agents are administered together, concurrently, or sequentially in one or more separate formulations.

In some embodiments, agent(s) that activate NRF2 signaling are administering before, during, or after mechanical ventilation or a combination thereof. In some embodiments, subjects undergoing mechanical ventilation and NRF2 activating therapy are monitored to determine the presence or absence of symptoms of VILL In some embodiments, the dose or frequency of administration of the NRF2 activating agent is adjusted (e.g., increased, described, or stopped) based on the presence or absence of symptoms of VILI.

In some embodiments, NRF2 activating agents are administered systemically (e.g., orally or intravenously) or directly to the lung (e.g., via pulmonary delivery). Exemplary delivery methods are described below.

While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being at risk for VILI.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

A pharmaceutical composition may be administered in the form, which is formulated with a pharmaceutically acceptable carrier and optional excipients, adjuvants, etc. in accordance with good pharmaceutical practice. The pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. pill, injection, etc.), the composition form is determined. In general, it is preferred to use a unit dosage form in order to achieve an easy and accurate administration of the active pharmaceutical agent. In general, the therapeutically effective pharmaceutical compound is present in such a dosage form at a concentration level ranging from about 0.5% to about 99% by weight of the total composition, e.g., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, a pharmaceutical composition is provided in a unit dosage form for administration to a subject, comprising a peptides or polypeptide and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

NRF2 activating agents (e.g., bixin) may be further derivatized by chemical alterations, such as amidation, glycosylation, acylation, sulfation, phosphorylation, acetylation, and cyclization. Such chemical alterations can be imparted through chemical or biochemical methodologies, as well as through in vivo processes, or any combination thereof.

The NRF2 activating agents (e.g., bixin) described herein may be prepared as salts with various inorganic and organic acids and bases. Such salts include salts prepared with organic and inorganic acids, for example, with HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, alkali earth salts, e.g. calcium and magnesium salts, and zinc salts. The salts may be formed by conventional means, such as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The NRF2 activating agents (e.g., bixin) described herein can be formulated as pharmaceutically acceptable salts and/or complexes thereof. Pharmaceutically acceptable salts include acid addition salts such as those containing sulfate, hydrochloride, phosphate, sulfamate, acetate, citrate, lactate, tartrate, succinate, oxalate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The NRF2 activating agents (e.g., bixin) described herein may be formulated as pharmaceutical compositions for use in conjunction with the methods of the present disclosure. Compositions disclosed herein may conveniently be provided in the form of formulations suitable for parenteral administration, including subcutaneous, intramuscular and intravenous administration, nasal administration, pulmonary administration, or oral administration. Suitable formulation of peptides and polypeptides for each such route of administration is described in standard formulation treatises, e.g., Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1988).

Certain of the NRF2 activating agents (e.g., bixin) described herein may be substantially insoluble in water and sparingly soluble in most pharmaceutically acceptable protic solvents and in vegetable oils. In certain embodiments, cyclodextrins may be added as aqueous solubility enhancers. Cyclodextrins include methyl, dimethyl, hydroxypropyl, hydroxyethyl, glucosyl, maltosyl and maltotriosyl derivatives of alpha-, beta-, and gamma-cyclodextrin. An exemplary cyclodextrin solubility enhancer is hydroxypropyl-beta-cyclodextrin (HPBCD), which may be added to any of the above-described compositions to further improve the aqueous solubility characteristics of the peptides or polypeptides. In one embodiment, the composition comprises 0.1% to 20% HPBCD, 1% to 15% HPBCD, or from 2.5% to 10% HPBCD. The amount of solubility enhancer employed will depend on the amount of agent of the present disclosure in the composition. In certain embodiments, the peptides may be formulated in non-aqueous polar aprotic solvents such as DMSO, dimethylformamide (DMF) or N-methylpyrrolidone (NMP).

In some cases, it will be convenient to provide the NRF2 activating agents (e.g., bixin) and another active agent in a single composition or solution for administration together. In other cases, it may be more advantageous to administer the additional agent separately from said NRF2 activating agents (e.g., bixin).

For use, pharmaceutical compositions of the peptides and polypeptides described herein may be provided in unit dosage form containing an amount of the agent effective for a single administration. Unit dosage forms useful for subcutaneous administration include prefilled syringes and injectors.

In certain embodiments, the NRF2 activating agents (e.g., bixin) are administered in an amount, expressed as a daily equivalent dose regardless of dosing frequency, of 50 micrograms ("mcg") per day, 60 mcg per day, 70 mcg per day, 75 mcg per day, 100 mcg per day, 150 mcg per day, 200 mcg per day, or 250 mcg per day. In some embodiments, the polypeptide is administered in an amount of 500 mcg per day, 750 mcg per day, or 1 milligram ("mg") per day. In yet further embodiments, the NRF2 activating agents (e.g., bixin) are administered in an amount, expressed as a daily equivalent dose regardless of dosing frequency, of 1-10 mg per day, including 1 mg per day, 1.5 mg per day, 1.75 mg per day, 2 mg per day, 2.5 mg per day, 3 mg per day, 3.5 mg per day, 4 mg per day, 4.5 mg per day, 5 mg per day, 5.5 mg per day, 6 mg per day, 6.5 mg per day, 7 mg per day, 7.5 mg per day, 8 mg per day, 8.5 mg per day, 9 mg per day, 9.5 mg per day, or 10 mg per day. In various embodiments, the NRF2 activating agents (e.g., bixin) are administered on a monthly dosage schedule. In other embodiments, the NRF2 activating agents (e.g., bixin) are administered biweekly. In yet other embodiments, the NRF2 activating agents (e.g., bixin) are administered weekly. In certain embodiments, the NRF2 activating agents (e.g., bixin) are administered daily ("QD"). In select embodiments, the NRF2 activating agents (e.g., bixin) are administered twice a day ("BID").

In some embodiments, the NRF2 activating agents (e.g., bixin) are administered for at least 3 months, at least 6 months, at least 12 months, or more. In some embodiments, the agents are administered for at least 18 months, 2 years, 3 years, or more.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler or via ventilators. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 .mu.m. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 to Lloyd et al. and WO 97/12687 (Eicher et al.).

In another specific embodiment of this invention, the pharmaceutical composition comprising the active agent is administered by inhalation using a dry powder inhaler. Such dry powder inhalers typically administer the active agent as a free-flowing powder that is dispersed in a patient's airstream during inspiration. In order to achieve a free flowing powder, the active agent is typically formulated with a suitable excipient such as lactose or starch.

A representative pharmaceutical composition for use in a dry powder inhaler comprises dry lactose having a particle size between about 1 µm and about 100 µm and micronized particles of the agent, or a pharmaceutically acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237 to Newell et al.); Diskus (GlaxoSmithKline) (see, e.g., U.S. Pat. No. 6,378,519 to Davies et al.); Turbuhaler (AstraZeneca, Wilmington, Del.) (see, e.g., U.S. Pat. No. 4,524,769 to Wetterlin); Rotahaler (GlaxoSmithKline) (see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt or solvate or stereoisomer thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company).

A representative pharmaceutical composition for use in a metered-dose inhaler comprises from about 0.01% to about 5% by weight of a compound of agent, or a pharmaceutically acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.).

For additional examples of processes of preparing respirable particles, and formulations and devices suitable for inhalation dosing see U.S. Pat. No. 6,268,533 to Gao et al., U.S. Pat. No. 5,983,956 to Trofast, U.S. Pat. No. 5,874,063 to Briggner et al., and U.S. Pat. No. 6,221,398 to Jakupovic et al.; and WO 99/55319 (Glaxo Group Ltd.) and WO 00/30614 (AstraZeneca AB).

In some embodiments, provided herein are methods for treating patients suffering from (or at risk of) VILI and/or in need of treatment (or preventative therapy).

In some embodiments, a pharmaceutical composition comprising at least one NRF2 activating agent (e.g., bixin) described herein is delivered to such a patient in an amount and at a location sufficient to treat the condition. In some embodiments, agents (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application methods of treating a patient most preferably substantially alleviates or even eliminates such symptoms; however, as with many medical treatments, application of the inventive method is deemed successful if, during, following, or otherwise as a result of the inventive method, the symptoms of the disease or disorder in the patient subside to an ascertainable degree.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

Materials and Methods

Chemicals, Antibodies, and Cell Culture

Bixin, tBHQ, and sodium arsenite (As(III)) were purchased from Sigma, and sulforaphane (SF) was from Santa Cruz. Primary antibodies against NRF2, KEAP1, GCLM, HO-1, GAPDH, and the hemagglutinin (HA) epitope, as well as horseradish peroxidase (HRP)-conjugated secondary antibodies were from Santa Cruz. Antibodies against p-P65 and P65 were from Cell Signaling, and the 8-oxo-dG antibody was from Trevigen. The Alexa Fluor 488-conjugated secondary antibody was from Invitrogen. The human non-small cell carcinoma H1299 cells were purchased from ATCC and were grown in RPMI 1640 medium supplemented with 10% FBS (Atlanta Biological) and 0.1% gentamycin (Invitrogen). Normal human bronchial epithelial cells (NHBE) and normal lung microvascular endothelial cells (HMVEC-L) were purchased from Lonza and were grown in Bronchial Epithelial Growth Medium (BEGM, Lonza) and Endothelial Cell Growth Medium (EGM, Lonza), respectively, according to the supplier's instructions. All cells were maintained at 37° C. in a humidified incubator containing 5% $CO_2$.

Transfection of siRNA, cDNA, and Luciferase Reporter Gene Assay

Transfection of small interfering RNA (Control siRNA #1027281, KEAP1 siRNA #SI03246439, Qiagen) was performed using HiPerfect (Qiagen) according to the manufacturer's instructions. Transfection of cDNA was performed 24 h after siRNA transfection using Lipofectamine 3000 (Invitrogen) according to the manufacturer's instructions. Activation of NRF2 transcriptional activity was performed as previously published (Wang, X. J. et al. Activation of Nrf2 by arsenite and monomethylarsonous acid is independent of Keap1-C151: enhanced Keap1-Cul3 interaction. Toxicol Appl Pharmacol 230, 383-9 (2008)). Briefly, H1299 cells were cotransfected with expression vectors for either KEAP1 wild type (KEAP1-WT) or a mutant KEAP1 (KEAP1-C151S), along with mGst-ARE firefly and Renilla luciferase reporters. At 24 h post-transfection, cells were treated with SF (5 µM), tBHQ (50 µM), As (5 µM), or bixin (40 µM) for 16 h, then lysed for analysis of the reporter gene activity using the Promega dual-luciferase reporter gene assay system.

Cell Viability

Bixin toxicity was measured by functional impairment of the mitochondria using 3-(4,5-dimethylthiazol-2-yl)-2,5-diphenyltetrazolium bromide (MTT) (Sigma). Cells ($1\times10^4$) were seeded in a 96-well plate; 24 h later the cells were treated with the indicated doses of bixin for 48 h. 20 µL of 2 mg/mL MTT were directly added to the cells which were then incubated at 37° C. for 2 h. 100 µl of isopropanol/HCl were added to each well and the plate was shaken at room temperature (RT). Absorbance was measured at 570 nm using the Synergy 2 Multi-Mode Microplate Reader (Biotek).

Immunoblot Analysis, Ubiquitylation Assay, and Protein Half Life

H1299 cells were harvested in sample buffer (50 mM Tris-HCl [pH 6.8], 2% SDS, 10% glycerol, 100 mM DTT, and 0.1% bromophenol blue), boiled and sonicated. Total cell lysates were resolved by SDS-PAGE and subjected to immunoblot analyses with the indicated antibodies. For the ubiquitination assay, cells were cotransfected with expression vectors for NRF2 and HA-tagged ubiquitin (HA-Ub), or with KEAP1 siRNA plus KEAP1-WT or KEAP1-C151S. The cells were left untreated or treated with either SF (5 µM) or bixin (40 µM) along with MG132 (10 µM) for 4 h. The cells were harvested in buffer containing 2% SDS, 150 mM NaCl, 10 mM Tris-HCl (pH 8.0), and 1 mM DTT and boiled. For immunoprecipitation, 1 µg of NRF2 antibody was incubated with the cell lysates at 4° C. overnight with protein A agarose beads (Invitrogen). Immunoprecipitated complexes were washed four times with RIPA buffer and eluted in sample buffer by boiling for 5 min. Samples were resolved by SDS-PAGE and immunoblotted with HA or Ub antibodies. To measure the half-life of NRF2, H1299 cells were either left untreated or treated with bixin (5 µM) for 4 h, then cycloheximide (50 µM) was added to block protein synthesis. Total cell lysates were collected at different time points and subjected to immunoblot analysis with NRF2 antibody. The relative intensity of the bands was quantified using the ChemiDoc CRS gel documentation system and Quantity One software (BioRad).

mRNA Extraction and Real-Time RT-PCR

Total RNA was extracted from H1299 cells and mouse lung tissues using TRIzol (Invitrogen). Equal amounts of mRNA were used to generate cDNA using the M-MLV Reverse Transcriptase synthesis kit according to the manufacturer's instructions (Promega). RT-PCR and primer sequences of NRF2, KEAP1, GCLM, HMOX1 and GAPDH were described previously (Tao, S. et al. Tanshinone I activates the Nrf2-dependent antioxidant response and protects against As(III)-induced lung inflammation in vitro and in vivo. Antioxid Redox Signal 19, 1647-61 (2013)) to evaluate mRNA expression using the LightCycler 480 system (Roche). Quantification of cDNA amount for mouse Nrf2, Keap1, Gclm, and Hmox1 in each lung tissue sample was performed with KAPA SYBR FAST qPCR Kit (Kapa Biosystems). Primers were designed with Primer 3 and synthesized by Sigma as follows:

```
Nrf2:
forward
(CTCAGCATGATGGACTTGGA; SEQ ID NO: 1)

reverse
(TCTTGCCTCCAAAGGATGTC; SEQ ID NO: 2);

Keap1:
forward
(GATCGGCTGCACTGAACTG; SEQ ID NO: 3)

reverse
(GGCAGTGTGACAGGTTGAAG; SEQ ID NO: 4);

Hmox1:
forward
(GAGCCTGAATCGAGCAGAAC; SEQ ID NO: 5)

reverse
(CTCGGCTTGGATGTGTACCT; SEQ ID NO: 6);

Gclm:
forward
(TCCCATGCAGTGGAGAAGAT; SEQ ID NO: 7)

reverse
(AGCTGTGCAACTCCAAGGAC; SEQ ID NO: 8);

β-actin:
forward
(AAGGCCAACCGTGAAAAGAT; SEQ ID NO: 9)

reverse
(GTGGTACGACCAGAGGCATAC; SEQ ID NO: 10).
```

The real-time PCR conditions used were: initial denaturation (95° C., 3 min), 40 cycles of amplification (95° C., 10 s; 60° C., 20 s; 72° C., 5 s), melting curve (95° C., 5 s; 65° C., 1 min; 97° C. continuous), and cooling cycle (40° C., 30 s). Mean crossing point (Cp) values and standard deviations (SD) were determined. Cp values were normalized to the respective Cp values of the mouse β-actin reference gene. Data are presented as a fold change in gene expression compared to the control group.

Animals and Treatments

Nrf2$^{+/+}$ and Nrf2$^{-/-}$ SKH-I mice were obtained by breeding Nrf2$^{+/-}$ mice. All animals received water and food ad libitum, were handled according to the Guide for the Care and Use of Laboratory Animals, and the protocols were approved by the University of Arizona Institutional Animal Care and Use Committee. Eight-week-old Nrf2$^{+/+}$ and Nrf2$^{-/-}$ mice were randomly allocated into four groups (n=6): (i) control (corn oil); (ii) bixin (200 mg/kg, dissolved in corn oil); (iii) ventilation; (iv) bixin+ventilation. Bixin was administrated through intraperitoneal (IP) injection 72 h before ventilation. For ventilation-induced lung injury (VILI) experiments, mice were subjected to mechanical ventilation (Moreno-Vinasco, L. et al. Nicotinamide phosphoribosyltransferase inhibitor is a novel therapeutic candidate in murine models of inflammatory lung injury. Am J Respir Cell Mol Biol 51, 223-8 (2014). Briefly, mice were anesthetized with ketamine/xylazine (IP, 100/5 mg/kg, respectively), intubated with a 20-gauge IV catheter, and connected to the ventilator (Inspira, Harvard Apparatus). The ventilation parameters using room air were: tidal volume 40 mL/kg, respiratory rate 75 breaths/min, and a positive and expiratory pressure of 0 cm $H_2O$ for 4 h. Mice were constantly monitored and deep anesthesia was maintained throughout the experiment with ketamine/xylazine. Mice in the control and bixin groups were allowed to breathe spontaneously. All mice survived the ventilation treatment and/or bixin injections.

Bronchoalveolar Lavage (BAL) and Lung Tissue Collection

After the treatments, mice were euthanized and BAL fluid was obtained by lavaging the lung with 1 mL HBSS (Invitrogen) through the tracheal cannula (Moreno-Vinasco, L. et al. Nicotinamide phosphoribosyltransferase inhibitor is a novel therapeutic candidate in murine models of inflammatory lung injury. Am J Respir Cell Mol Biol 51, 223-8 (2014). The BAL fluid was centrifuged at 500×g for 20 min at 4° C. to collect the cells. Cell pellets were resuspended in PBS and total cell counts were determined using the TC20 automated cell counter (BioRad). Cytospins of BAL cells were prepared (Cytospin 4, Thermo Fisher Scientific) and slides were stained with the Shandon Kwik-Diff kit (Thermo Fisher Scientific). Macrophages and neutrophils were identified using the standard morphologic criteria; 200 cells were examined per sample. The mean cell counts±SD were obtained from 6 mice of each group. The supernatant collected from the BAL fluid was centrifuged again at 15,000×g for 10 min at 4° C. and stored at −80° C. until used for protein analysis. Lungs were collected and divide: one part was frozen in liquid nitrogen for total RNA extraction and protein analysis; the other part was fixed in 10% buffered formalin and embedded in paraffin for histological and immunochemical analyses.

HE Staining and IHC

Tissue sections (4 μm) were baked and deparaffinized. Hematoxylin and eosin (HE) staining was performed for pathological examination. IHC analysis was performed as previously described (Tao, S. et al. Tanshinone I activates the Nrf2-dependent antioxidant response and protects against As(III)-induced lung inflammation in vitro and in vivo. Antioxid Redox Signal 19, 1647-61 (2013)). Briefly, antigen retrieval was performed by boiling the slides with retrieval solution (citric acid monohydrate 2.1 g/L in $H_2O$, pH=6.0) three times for 5 min. Tissue sections were then exposed to 3.5 M HCl for 15 min at room temperature and washed with PBS. Subsequently, tissue sections were treated with 0.3% peroxidase to quench endogenous peroxidase activity. Tissue sections were incubated with 5% normal goat serum for 30 min followed by 2 h incubation with NRF2 antibody at 1:100 dilution at RT. Staining was performed using the EnVision+System-HRP kit (Dako) according to the manufacturer's instructions.

Enzyme-Linked Immunosorbent Assay (ELISA) of Cytokines in BAL Fluid

The ELISA kit (eBiosciences) was used according to the manufacturer's instructions. Briefly, the plate was coated with 100 μL capture antibody in coating buffer per well and incubated overnight. The plate was washed with 250 μL wash buffer, blocked with 200 μL of the assay diluents, and incubated for 1 h. BAL fluid (100 μL) was added and incubated for 2 h, then 100 μL of detection antibody (IL-6, TNFα) was added to each well and incubated for 1 h. Subsequently, 100 μL avidin-HRP was added and the plate was incubated for 30 min. 100 μL of the substrate solution was added to each well and incubated for 15 min; the reaction was stopped with 50 μL of stop solution. All incubations were done at RT. The plate was read at 450 nm.

Indirect Immunofluorescence

H1299 cells were seeded on glass cover slips, 24 h were treated with bixin (40 μM) for the indicated time points. Cells were fixed with chilled methanol and incubated with anti-NRF2 antibody, then with an Alexa Fluor 488-conjugated secondary antibody. Nuclei were counterstained with DAPI. Images were obtained using a Zeiss Observer.Z1 microscope with the Slidebook 5.0 software (Intelligent Imaging Innovations).

Statistics

Results are presented as the mean±SD of three independent experiments performed in duplicate (real-time RT-PCR) or triplicate. Statistical tests were performed using SPSS 13.0. Unpaired Student's t-tests were used to compare the means of two groups. One-way ANOVA with Bonferroni's correction was used to compare the means of three or more groups. P<0.05 was considered to be significant.

Example 2

Figure 7:
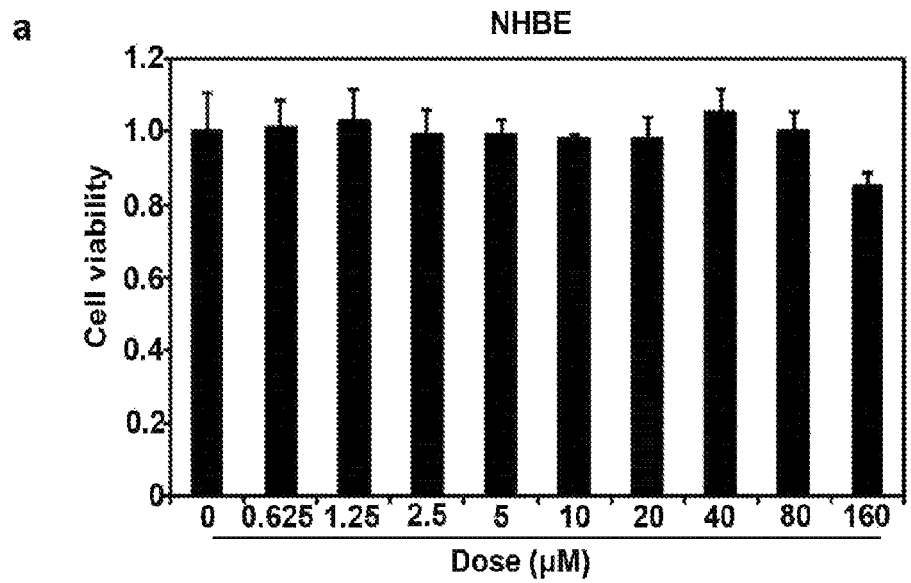
FIG. 7 shows bixin cytotoxicity in primary human cell lines. Cell viability was measured in (a) normal human bronchial epithelial cells (NHBE) and (b) normal lung microvascular endothelial cells (HMVEC-L) treated with the indicated doses of bixin for 48 h.
Figure 7:
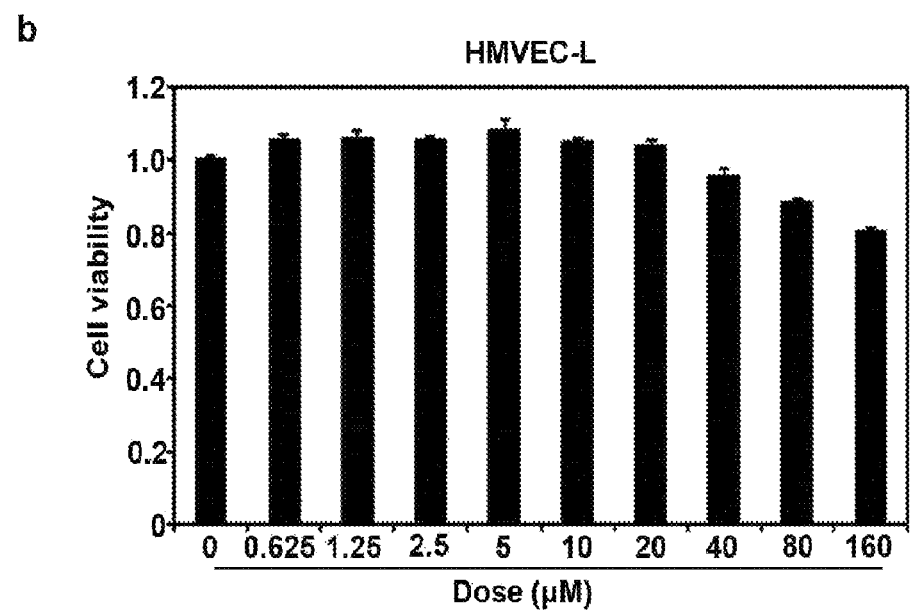

Bixin Induces the NRF2 Signaling Pathway with No Detectable Toxicity Under a Wide Dose Range Based on the chemical structure of bixin (FIG. 1a), it was investigated if bixin was able to induce the Nrf2 signaling pathway in lung cells. An MTT assay was first employed to determine bixin cytotoxicity in cells treated for 48 h with doses ranging from 0.625-160 μM. In normal primary bronchial epithelial (NHBE), no cytotoxicity was observed at any of the doses tested, whereas in lung microvascular endothelial cells (HMVEC-L) there was a slight decrease in viability (20%) at the highest dose tested (FIG. 7). In immortalized normal bronchial epithelial cells (HBE and BEAS-2B) and the lung cancer cell line H1299 (FIG. 1b), no cytotoxicity was found at any of the doses tested. These results demonstrate that bixin is a well-tolerated compound in cells of the lower respiratory system.

Figure 8:
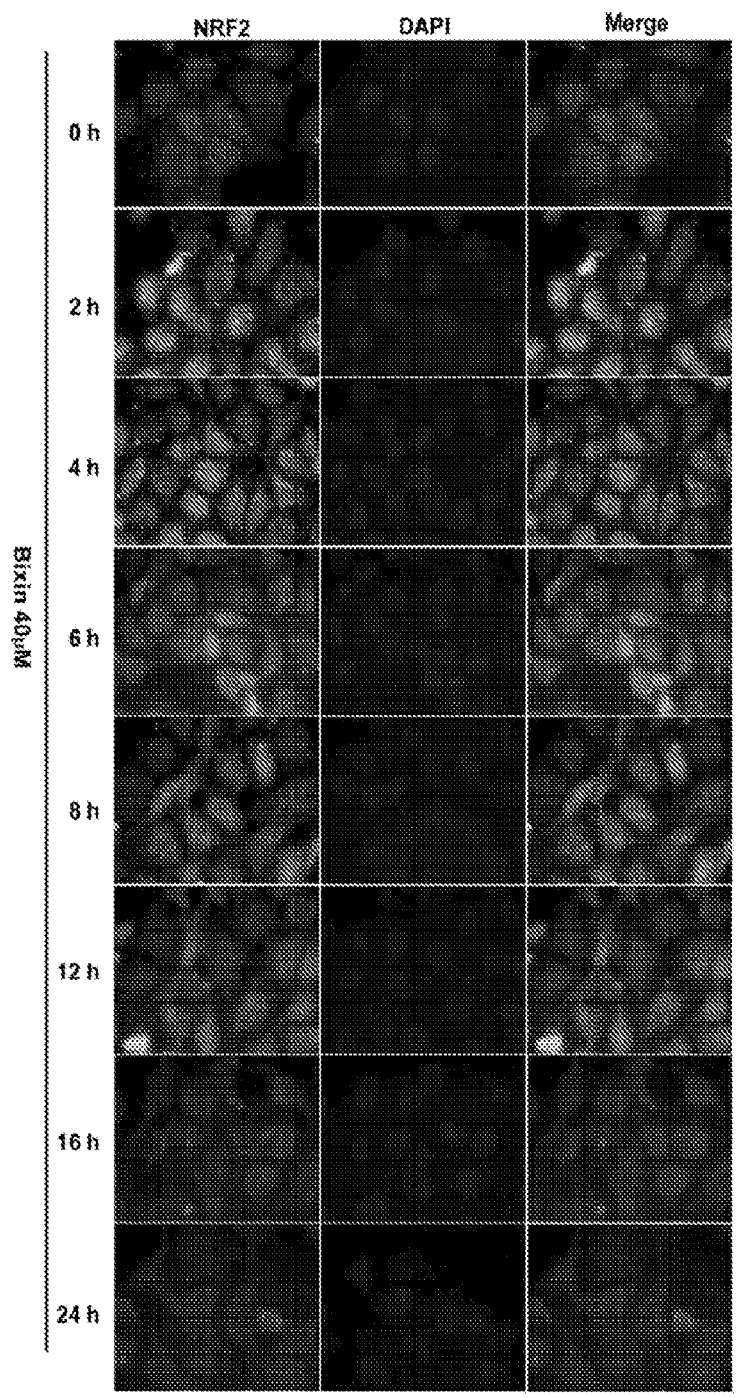
FIG. 8 shows images of H1299 cells that were treated with bixin (40 µM) for the indicated time points, fixed and stained.

Three doses of bixin (10, 20, and 40 μM) were chosen to test their ability to induce the NRF2 signaling pathway in H1299 cells. Immunoblotting analyses show that there was a dose-response effect in the induction of NRF2 protein levels after a 4 h treatment and of its downstream targets HO-1 and GCLM after a 16 h treatment, while no effects were observed on KEAP1 expression levels (FIG. 1c). Since the highest induction was obtained with 40 μM bixin, this dose was then used for a time course study. NRF2 protein levels were significantly induced as early as 2 h after treatment, reaching its highest levels between 2-4 h and returning to basal levels by 24 h (FIG. 1d). This protein induction correlates with increased cytoplasmic and nuclear accumulation of NRF2 (FIG. 8). In addition, GCLM protein levels increased at 8 h and peaked between 12 and 24 h, with persistent elevation up to 48 h after treatment. No change was observed in KEAP1 protein levels. Furthermore, 40 µM bixin treatment for either 4 or 16 h did not affect the mRNA levels of NRF2 nor KEAP1 (FIG. 1e), consistent with previous observations for canonical NRF2 inducers (Wang, X. J. et al. Activation of Nrf2 by arsenite and monomethylarsonous acid is independent of Keap1-C151: enhanced Keap1-Cul3 interaction. Toxicol Appl Pharmacol 230, 383-9 (2008)). In contrast, the mRNA levels of both HMOXJ and GCLM increase significantly after the treatment. These results indicate that bixin is a non-cytotoxic inducer of the NRF2 signaling pathway.

Example 3

Bixin is a Canonical NRF2 Inducer that Activates NRF2 in a KEAP1-C151-Dependent Manner The mechanism by which bixin activates the NRF2 pathway was explored, although the present invention is not limited to any particular mechanism. NRF2 inducers cause NRF2 activation by inhibiting its KEAP1-mediated ubiquitination (Tao, S. et al. Tanshinone I activates the Nrf2-dependent antioxidant response and protects against As(III)-induced lung inflammation in vitro and in vivo. Antioxid Redox Signal 19, 1647-61 (2013); Wondrak, G. T. et al. The cinnamon-derived dietary factor cinnamic aldehyde activates the Nrf2-dependent antioxidant response in human epithelial colon cells. Molecules 15, 3338-55 (2010). Therefore, a cell-based ubiquitination assay was performed in H1299 cells cotransfected with expression vectors for NRF2 and HA-tagged ubiquitin (HA-Ub). The cells were either left untreated or treated with SF (5 µM, as a positive control) or bixin (40 µM), along with the protease inhibitor MG132 (100 µM) for 4 h. Bixin treatment markedly reduced the ubiquitination level of NRF2 compared to the untreated control; as expected, SF treatment also decreased NRF2 ubquitination (FIG. 2a).

Next was determined if bixin is a canonical Nrf2 inducer. H1299 cells were first transfected with KEAP1-siRNA to knockdown endogenous protein (FIG. 9a) and 24 h later were cotransfected with expression vectors for either KEAP1 wild type (KEAP1-WT) or a KEAP1 where the cysteine 151 was mutated to serine (KEAP1-C151S). The cells were then either left untreated or treated with bixin (40 µM) along with MG132 (100 µM) for 4 h, and the cell lysates were used for a ubiquitination assay. Bixin prevented the ubiquitination of cells with endogenous KEAP1 or expressing exogenous KEAP1-WT but had no effect on cells expressing KEAP1-C151S (FIG. 2b). To further confirm that bixin is a canonical NRF2 inducer, endogenous expression of KEAP1 was knocked down in H1299 cells. The cells were then cotransfected with KEAP1-WT or KEAP1-C151S plasmids as well as with ARE-firefly luciferase and Renilla luciferase reporters to assess NRF2 transcriptional activity. Cells were treated with SF (5 µM), tBHQ (50 µM), As(III) (5 µM), and bixin (40 µM) for 16 h. NRF2 transcriptional activity was enhanced by all treatments in KEAP1-WT cells, while in KEAP1-C151S cells NRF2 activation by SF, tBHQ, or bixin was inhibited (FIG. 2c). In contrast, arsenic treatment was still able to induce NRF2 transcriptional activity in the KEAP1-C151S cells consistent with previous finding that arsenic is a non-canonical NRF2 inducer that works through a KEAP1 C151-independent mechanism (Lau, A. et al. A noncanonical mechanism of Nrf2 activation by autophagy deficiency: direct interaction between Keap1 and p62. Mol Cell Biol 30, 3275-85 (2010)). Taken together, these results demonstrate that bixin is a canonical NRF2 inducer that acts through the critical C151 sensor residue in KEAP1.

Figure 9:
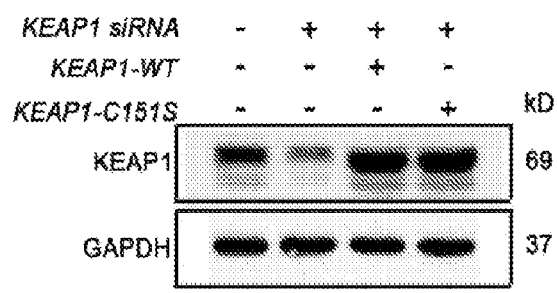
FIG. 9 shows (a) H1299 cells transfected with siRNA and 24 h later transfected with plasmids encoding for KEAP1-WT or KEAP1-C151S for another 24 h. (b) H1299 cells were transfected with siRNA and 24 h later were transfected with plasmids encoding for KEAP1-WT or KEAP1-C151S.
Figure 9:
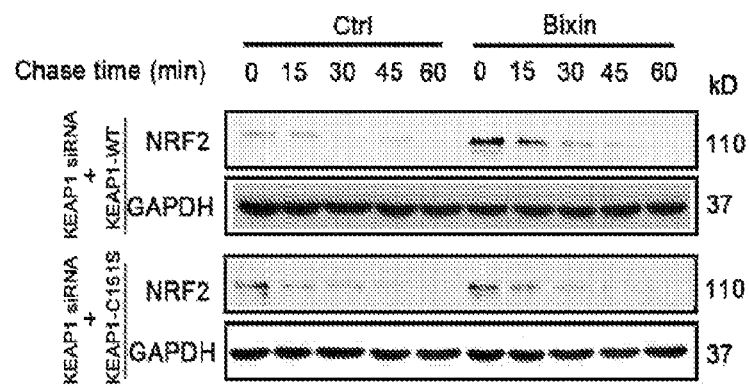

Next, the half-life of endogenous NRF2 protein was determined. Cycloheximide was added to untreated or bixin-treated H1299 cells to block de novo protein synthesis and cells were harvested at different time points. The protein levels of NRF2 were detected by immunoblot analysis (FIG. 2d, left panel) and the intensity of the NRF2 band was quantified and plotted to calculate the half-life of NRF2 (FIG. 2d, right panel). The half-life of NRF2 of untreated cells was 19.4 min; however, after bixin treatment the half-life of NRF2 increased to 28.9 min. This increase in NRF2 half-life is also KEAP1-C151-dependent (FIG. 9b). These results indicate that bixin activates NRF2 by decreasing its ubiquitination and increasing NRF2 protein stability in a KEAP1-C151-dependent manner.

Example 4

Figure 10:
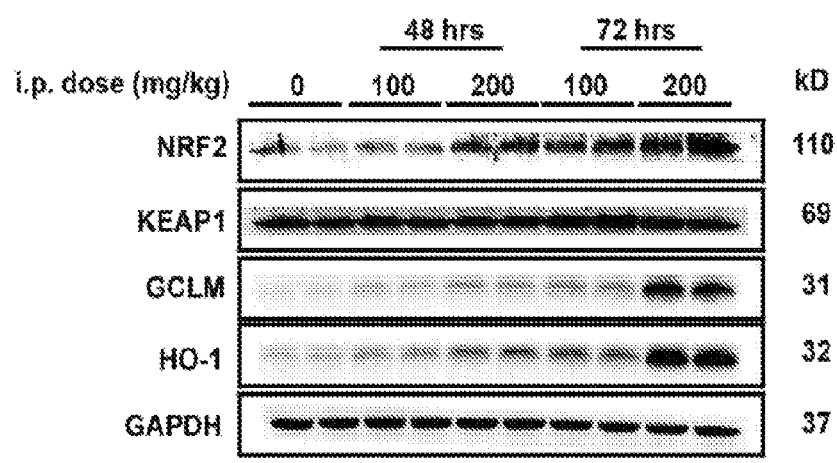
FIG. 10 shows pulmonary NRF2 signaling pathway activation by IP injection of bixin.

IP Injection of Bixin Activates the NRF2 Signaling Pathway and Suppresses the NF-κB Inflammatory Response in the Lungs of Nrf2$^{+/+}$ Mice A pilot study to test the bixin treatment regimen (dose and injection duration) that resulted in the maximum activation of the NRF2 signaling pathway in the lung was performed. IP injection of bixin (200 mg/kg, 72 h) was effective in upregulating pulmonary protein levels of NRF2 and its target genes (Gclm and Hmox1) in Nrf2$^{+/+}$ mice as measured by immunoblot analysis (FIG. 10). This treatment regimen was then used throughout the study.

The protective activity of bixin was studied in a ventilation-induced lung injury (VILI) model. Nrf2$^{+/+}$ and Nrf2$^{-/-}$ mice were IP injected with either corn oil (vehicle control, Ctrl) or bixin (200 mg/kg) 72 h before being subjected to high tidal volume ventilation (40 mL/kg) for 4 h. Lung tissues were collected immediately after ventilation and subjected to immunohistochemistry (IHC) analyses. Indeed, bixin treatment was able to increase NRF2 protein levels (FIG. 3a) as well as HO-1 and GCLM (FIGS. 3b and c, respectively) in Nrf2$^{+/+}$ mice lungs. Ventilation alone dramatically induced the NRF2 pathway in Nrf2$^{+/+}$ mice (Papaiahgari, S. et al. Genetic and pharmacologic evidence links oxidative stress to ventilator-induced lung injury in mice. Am J Respir Crit Care Med 176, 1222-35 (2007); Mirzapoiazova, T. et al. Non-muscle myosin light chain kinase isoform is a viable molecular target in acute inflammatory lung injury. Am J Respir Cell Mol Biol 44, 40-52 (2011); Reiss, L. K. et al. Interplay between nuclear factor erythroid 2-related factor 2 and amphiregulin during mechanical ventilation. Am J Respir Cell Mol Biol 51, 668-77 (2014)) (FIG. 3). Moreover, when the Nrf2$^{+/+}$ mice were treated with bixin and ventilation, the NRF2 pathway was also activated (FIG. 3). In contrast, Nrf2$^{-/-}$ mice had no detectable NRF2 and both the basal and inducible levels of HO-1 and GCLM were very low compared to Nrf2$^{+/+}$ mice (FIG. 3). Furthermore, immunoblot analyses of total protein extracted from these lung tissues revealed that bixin and ventilation, alone or in combination, can induce NRF2, HO-1 and GCLM in Nrf2$^{+/+}$ mice without affecting KEAP1 (FIG. 4a). Since one of the main side effects of ventilation is exacerbated inflammation, the activation of the NF-κB pathway was investigated by detecting phosphorylation of the p65 subunit. While total levels of p65 were unaffected, the phosphorylated (active) form of P65 (p-P65) was markedly induced by ventilation in both $Nrf2^{+/+}$ and $Nrf2^{-/-}$ mice (FIG. 4b). However, bixin pretreatment decreased p-P65 accumulation in $Nrf2^{+/+}$ mice, which may be due to the activation of NRF2, with very minimal effects in $Nrf2^{-/-}$ mice (FIG. 4b). To further corroborate these results, mRNA levels of Nrf2, Keap1, Hmox1 and Gclm were also assessed (FIGS. 4c-f). The mRNA levels of Nrf2 did not increase in the treatment groups, which is consistent with the in vitro results demonstrating that bixin activates NRF2 by stabilizing its protein levels (FIG. 4c). Bixin had no effects on the mRNA levels of Keap1 (FIG. 4d). Although Hmox1 and Gclm had similar basal mRNA levels in $Nrf2^{+/+}$ and $Nrf2^{-/-}$ mice they were only induced after treatment with either bixin, ventilation, or the combination in $Nrf2^{+/+}$ mice (FIGS. 4e and 4f).

Example 5

Bixin Restored Normal Lung Morphology and Attenuated Inflammatory Response and Oxidative DNA Damage in the Lungs of $Nrf2^{+/+}$ but not $Nrf2^{-/-}$ Mice Following MV Treatment Hematoxylin and eosin (HE) staining of lung tissues revealed infiltration of inflammatory cells and alveolar septal thickening in the lungs of both $Nrf2^{+/+}$ and $Nrf2^{-/-}$ mice after 4 h ventilation (FIG. 5a). Bixin injection alone did not affect the lung morphology of mice of either genotype but dramatically attenuated the pulmonary pathological alterations caused by ventilation in $Nrf2^{+/+}$ mice, whereas no improvement was observed in the lungs from $Nrf2^{-/-}$ mice (FIG. 5a). In addition, IHC analysis for 8-hydroxy-2'-deoxyguanosine (8-oxo-dG) was performed to detect ventilation-induced oxidative DNA damage. Ventilation markedly enhanced 8-oxo-dG staining in both $Nrf2^{+/+}$ and $Nrf2^{-/-}$ mice (FIG. 5b). In contrast, bixin treatment alone did not have any effect, indicating it has no pro-oxidant effects at the dose used. However, bixin pretreatment significantly suppressed 8-oxo-dG staining in the lungs from $Nrf2^{+/+}$ but not $Nrf2^{-/-}$ mice that received ventilation (FIG. 5b). These results indicate that bixin protects against ventilation-induced pulmonary damage by decreasing inflammation and oxidative DNA damage, both of which depended on activation of the NRF2 signaling pathway.

Bronchoalveolar lavage (BAL) fluid was analyzed for total BAL protein, total BAL cell number and ratio of neutrophils. Ventilation greatly increased the total BAL protein in the lungs from both $Nrf2^{+/+}$ and $Nrf2^{-/-}$ mice, which indicated that both genotypes underwent through a similar bronchoalveolar leak (FIG. 6a). Bixin alone did not affect the total protein levels of either mice, but it significantly decreased the total BAL protein in $Nrf2^{+/+}$ mice following high tidal volume ventilation (FIG. 6a), which indicates that bixin can suppress ventilation-induced pulmonary vascular leakage in an NRF2-dependent manner. Similarly, ventilation increased inflammatory leukocyte infiltration to the lungs as assessed by the total number of BAL cells and the ratio of neutrophils in both $Nrf2^{+/+}$ and $Nrf2^{-/-}$ mice (FIGS. 6b and 6c). Bixin treatment of unventilated mice did not affect the total cell number or the ratio of neutrophils. However, bixin pretreatment decreased ventilation-induced neutrophil infiltration (total cells and ratio of neutrophils) only in $Nrf2^{+/+}$ but not $Nrf2^{-/-}$ mice (FIGS. 6b and 6c), further supporting the anti-inflammatory role of NRF2 in bixin-mediated protection against VILI. Ventilation-induced neutrophil infiltration was more pronounced in $Nrf2^{-/-}$ mice (FIG. 6c), indicating the basal level of Nrf2 was sufficient to confer protection against MV-induced inflammatory cell infiltration. Moreover, the amount of inflammatory cytokines (IL6, TNFα) was measured by ELISA as surrogate markers for NF-κB signaling activation. Ventilation greatly induced the expression of IL6 and TNFα in both $Nrf2^{+/+}$ and $Nrf2^{-/-}$ mice while bixin pretreatment reduced the expression of both cytokines only in ventilated $Nrf2^{+/+}$ mice (FIGS. 6d and e). Collectively, these results indicate that bixin can decrease the pulmonary inflammatory response associated with ventilation through activation of the NRF2 pathway and attenuation of NF-κB signaling.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

What is claimed is:

1. A method of treating protecting against ventilator-induced lung injury, comprising:
   administering bixin to a subject prior to, during, or after mechanical ventilation.

2. The method of claim 1, wherein said bixin activates a NRF2-mediated response by inhibiting KEAP1-mediated ubiquitination of NRF2.

3. The method of claim 1, wherein said bixin is administered directly to the lungs of said subject.

4. The method of claim 1, wherein said bixin is administered systemically to said subject.

5. The method of claim 1, wherein said administering protects inflammation and oxidative DNA damage in said subject.

6. The method of claim 1, wherein said administering treats or protects acute lung injury in said subject.

7. The method of claim 1, wherein said subject has lung trauma, chronic obstructive pulmonary disease (COPD), acute respiratory distress syndrome (ARDS), apnea, severe asthma, or is under general anesthesia.

* * * * *